(12) United States Patent
Kahlbaugh

(10) Patent No.: US 12,027,274 B2
(45) Date of Patent: *Jul. 2, 2024

(54) HUMAN METABOLIC CONDITION MANAGEMENT

(71) Applicant: Bradley E. Kahlbaugh, Bloomington, MN (US)

(72) Inventor: Bradley E. Kahlbaugh, Bloomington, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/720,846

(22) Filed: Apr. 14, 2022

(65) Prior Publication Data

US 2022/0238234 A1 Jul. 28, 2022

Related U.S. Application Data

(63) Continuation of application No. 16/701,401, filed on Dec. 3, 2019, now Pat. No. 11,309,089, which is a continuation of application No. 15/518,834, filed as application No. PCT/US2015/055658 on Oct. 15, 2015, now Pat. No. 10,529,454.

(Continued)

(51) Int. Cl.
| | |
|---|---|
| *G16H 50/50* | (2018.01) |
| *A61B 5/00* | (2006.01) |
| *A61B 5/145* | (2006.01) |
| *A61M 5/142* | (2006.01) |
| *A61M 5/172* | (2006.01) |
| *G16H 20/10* | (2018.01) |
| *G16H 20/40* | (2018.01) |
| *G16H 20/60* | (2018.01) |
| *G16H 40/63* | (2018.01) |
| *G16H 50/30* | (2018.01) |

(52) U.S. Cl.
CPC ......... *G16H 50/50* (2018.01); *A61B 5/14532* (2013.01); *A61B 5/7275* (2013.01); *A61M 5/14244* (2013.01); *A61M 5/1723* (2013.01); *G16H 20/10* (2018.01); *G16H 20/40* (2018.01); *G16H 20/60* (2018.01); *G16H 40/63* (2018.01); *G16H 50/30* (2018.01); *A61M 2005/1726* (2013.01)

(58) Field of Classification Search
CPC ........ G16H 50/50; G16H 20/40; G16H 50/30; G16H 20/10; G16H 40/63; G16H 20/60; A61B 5/14532; A61B 5/7275; A61M 5/1723; A61M 2005/1726
USPC .......................................................... 705/2–3
See application file for complete search history.

(56) References Cited

U.S. PATENT DOCUMENTS 5,840,020 A 11/1998 Heinonen et al.
6,923,763 B1 8/2005 Kovatchev et al.
(Continued)

*Primary Examiner* — Michael Tomaszewski
(74) *Attorney, Agent, or Firm* — Billion & Armitage

(57) ABSTRACT

Systems and methods for extracting blood glucose patterns and suggesting a behavior may include receiving, at a computing device comprising a processor, temporal data including information regarding glucose readings; identifying, by the computing device, at least one pattern based on metabolite levels extracted from the temporal data the model including variables corresponding to each of the patterns; formulating, by the computing device, a model for predicting a metabolic response; and storing the model on a data storage device. Based on the model, the behavior may be suggested to maintain a blood glucose level within a desired range.

34 Claims, 27 Drawing Sheets

Related U.S. Application Data

(60) Provisional application No. 62/065,146, filed on Oct. 17, 2014.

(56) References Cited

U.S. PATENT DOCUMENTS

| | | |
|---|---|---|
| 9,202,009 B2 | 12/2015 | Seike et al. |
| 2003/0208113 A1 | 11/2003 | Mault et al. |
| 2006/0076025 A1* | 4/2006 | Kim .................. A23L 33/30 |
| | | 600/300 |
| 2007/0287144 A1* | 12/2007 | Kouchi ................ G16Z 99/00 |
| | | 703/11 |
| 2007/0288216 A1* | 12/2007 | Kouchi ................ G16H 50/50 |
| | | 703/11 |
| 2008/0108888 A1* | 5/2008 | Brown ............. G01N 33/48792 |
| | | 604/890.1 |
| 2011/0047108 A1 | 2/2011 | Chakrabarty et al. |
| 2011/0098548 A1* | 4/2011 | Budiman ............. G16Z 99/00 |
| | | 600/365 |
| 2011/0106011 A1 | 5/2011 | Cinar et al. |
| 2012/0288835 A1* | 11/2012 | Hayashi ............... G16H 50/50 |
| | | 434/236 |
| 2013/0132319 A1* | 5/2013 | Landers ................ G06N 5/02 |
| | | 706/46 |
| 2014/0032194 A1 | 1/2014 | Albisser et al. |
| 2014/0083868 A1 | 3/2014 | Zvikhachevskaya et al. |
| 2014/0235503 A1 | 8/2014 | Kim et al. |
| 2015/0347707 A1 | 12/2015 | Albisser et al. |
| 2015/0347708 A1 | 12/2015 | Albisser et al. |

* cited by examiner

| Meal | Description | n Serv | K Cal | g Sug. | g Star. | g Fat | g Pro. | g CFP |
|---|---|---|---|---|---|---|---|---|
| 1 | No Food | 0 | 0 | 0 | 0 | 0 | 0 | 0 |
| 2 | bread, 9 grain | 1 | 160 | 3 | 22 | 3.5 | 6 | 34.5 |
| 2 | peanut butter, | 1 | 190 | 3 | 3 | 16 | 7 | 29 |
| 2 | raisins, dried | 1 | 130 | 29 | 0 | 0 | 1 | 30 |
| 3 | cereal, cold, oat | 1.5 | 225 | 1.5 | 33 | 3.8 | 7.5 | 45.8 |
| 3 | walnut | 1 | 0 | 1 | 1 | 18 | 4 | 24 |
| 3 | raisins, dried | 1 | 130 | 29 | 0 | 0 | 1 | 30 |
| 3 | milk, whole | 2 | 300 | 24 | 0 | 16 | 16 | 56 |
| 4 | extra sharp | 1.6 | 160 | 0 | 1.4 | 12.8 | 11.2 | 24 |
| 4 | coto salami | 2 | 140 | 0 | 1.8 | 12 | 8 | 20 |
| 4 | bread, 9 grain | 1 | 160 | 3 | 22 | 3.5 | 6 | 34.5 |
| 4 | pickle, bread and | 1 | 30 | 7 | 1 | 0 | 0 | 7 |
| 5 | hot cereal, flax soy | 1 | 160 | 1 | 18 | 3 | 7 | 29 |
| 5 | walnut | 1 | 0 | 1 | 1 | 18 | 4 | 24 |
| 5 | raisins, dried | 1 | 130 | 29 | 0 | 0 | 1 | 30 |
| 5 | milk, whole | 1 | 150 | 12 | 0 | 8 | 8 | 28 |
| 6 | juice, orange, | 2 | 220 | 46 | 6 | 0 | 4 | 56 |
| 7 | bread, 9 grain | 1 | 160 | 3 | 22 | 3.5 | 6 | 34.5 |
| 7 | peanut butter, | 1.5 | 285 | 4.5 | 4.5 | 24 | 10.5 | 43.5 |
| 7 | raisins, dried | 1 | 130 | 29 | 0 | 0 | 1 | 30 |
| 7 | jelly, sugar free | 1.5 | 15 | 0 | 3 | 0 | 0 | 4.5 |
| 8 | peanut butter, | 1 | 190 | 3 | 3 | 16 | 7 | 29 |
| 8 | jelly, sugar free | 1 | 10 | 0 | 2 | 0 | 0 | 3 |
| 8 | bread, 9 grain | 1 | 160 | 3 | 22 | 3.5 | 6 | 34.5 |
| 8 | raisins, dried | 1 | 130 | 29 | 0 | 0 | 1 | 30 |
| 9 | butter sub, olive oil | 1 | 70 | 0 | 0 | 8 | 0 | 8 |
| 9 | egg, x large | 3 | 240 | 0 | 3 | 15 | 21 | 39 |
| 9 | bread, 9 grain | 1 | 160 | 3 | 22 | 3.5 | 6 | 34.5 |
| 9 | penut butter, | 1.5 | 285 | 4.5 | 4.5 | 24 | 10.5 | 43.5 |
| 10 | peach, canned | 3.5 | 210 | 38.5 | 7 | 0 | 3.5 | 49 |
| 11 | grapefruit | 2 | 120 | 22 | 4 | 0 | 2 | 28 |
| 12 | No Food | 0 | 0 | 0 | 0 | 0 | 0 | 0 |
| 13 | No Food | 0 | 0 | 0 | 0 | 0 | 0 | 0 |
| 14 | banana | 1 | 105 | 14 | 10 | 0 | 1 | 25 |

** CFP – grams of carbohydrate – fiber + fat + protein

*Fig. 13*

| Meal # | Sug. (g) | Sta. (g) | Fat (g) | Pro. (g) | SSFP (g) | Sug. % | Sta. % | Fat % | Pro. % | Ini BG (mg/dL) | Dose (U) |
|---|---|---|---|---|---|---|---|---|---|---|---|
| 1 | 0 | 0 | 0 | 0 | 0 | 0% | 0% | 0% | 0% | 311 | 6.5 |
| 2 | 35 | 25 | 20 | 14 | 94 | 37% | 27% | 21% | 15% | 112 | 4.0 |
| 3 | 56 | 34 | 38 | 29 | 156 | 36% | 22% | 24% | 18% | 205 | 13.0 |
| 4 | 10 | 26 | 28 | 25 | 86 | 12% | 31% | 33% | 29% | 254 | 9.0 |
| 5 | 43 | 19 | 29 | 20 | 111 | 39% | 17% | 26% | 18% | 179 | 11.0 |
| 6 | 46 | 6 | 0 | 4 | 56 | 82% | 11% | 0% | 7% | 55 | 0.0 |
| 7 | 37 | 30 | 28 | 18 | 113 | 32% | 26% | 24% | 16% | 269 | 12.0 |
| 8 | 35 | 27 | 20 | 14 | 97 | 36% | 28% | 20% | 15% | 199 | 8.0 |
| 9 | 8 | 30 | 51 | 38 | 125 | 6% | 24% | 40% | 30% | 198 | 9.5 |
| 10 | 39 | 7 | 0 | 4 | 49 | 79% | 14% | 0% | 7% | 119 | 7.0 |
| 11 | 22 | 4 | 0 | 2 | 28 | 79% | 14% | 0% | 7% | 102 | 6.0 |
| 12 | 0 | 0 | 0 | 0 | 0 | 0% | 0% | 0% | 0% | 388 | 13.0 |
| 13 | 0 | 0 | 0 | 0 | 0 | 0% | 0% | 0% | 0% | 451 | 15.0 |
| 14 | 14 | 10 | 0 | 1 | 25 | 56% | 40% | 0% | 4% | 263 | 13.0 |

\* Method: Blood glucose meter (BGM)

\*\* Drug: Novolog U100

\*\*\* Sta(rch) calculated from food label: total carbohydrate − fiber − sugar

\*\*\*\* SSFP calculated as Sugar + Starch + Fat + Protein

*Fig. 14*

| Meal # | meal meas # | date | Time | BGM glucose (mg/dL) |
|---|---|---|---|---|
| 1 | 1 | 131217 | 6:02 | 311 |
| 1 | 2 | 131217 | 7:05 | 293 |
| 1 | 3 | 131217 | 7:40 | 268 |
| 1 | 4 | 131217 | 8:06 | 219 |
| 1 | 5 | 131217 | 10:23 | 140 |
| 1 | 6 | 131217 | 11:22 | 139 |
| 2 | 1 | 131217 | 12:55 | 112 |
| 2 | 2 | 131217 | 13:45 | 143 |
| 2 | 3 | 131217 | 14:19 | 177 |
| 2 | 4 | 131217 | 15:15 | 172 |
| 2 | 5 | 131217 | 18:15 | 140 |
| 3 | 1 | 131218 | 7:00 | 205 |
| 3 | 2 | 131218 | 7:45 | 286 |
| 3 | 3 | 131218 | 8:25 | 301 |
| 3 | 4 | 131218 | 9:01 | 283 |
| 3 | 5 | 131218 | 11:02 | 146 |
| 3 | 6 | 131218 | 13:15 | 60 |
| 4 | 1 | 131218 | 19:50 | 254 |
| 4 | 2 | 131218 | 20:50 | 260 |
| 4 | 3 | 131218 | 21:45 | 183 |
| 4 | 4 | 131218 | 22:30 | 152 |
| 4 | 5 | 131218 | 23:55 | 107 |
| 5 | 1 | 131219 | 10:36 | 179 |
| 5 | 2 | 131219 | 11:38 | 210 |
| 5 | 3 | 131219 | 12:40 | 266 |
| 5 | 4 | 131219 | 13:25 | 230 |
| 5 | 5 | 131219 | 14:50 | 201 |

** No time lag between food and dose
** Exercise not logged

*Fig. 15A*

| Meal # | meal meas # | date | Time | BGM glucose (mg/dL) |
|---|---|---|---|---|
| 6 | 1 | 131219 | 3:55 | 55 |
| 6 | 2 | 131219 | 4:11 | 96 |
| 6 | 3 | 131219 | 4:25 | 170 |
| 6 | 4 | 131219 | 4:54 | 214 |
| 6 | 5 | 131219 | 6:04 | 208 |
| 6 | 5 | 131219 | 7:51 | 269 |
| 7 | 1 | 131220 | 7:55 | 269 |
| 7 | 2 | 131220 | 8:41 | 295 |
| 7 | 3 | 131220 | 9:54 | 333 |
| 7 | 4 | 131220 | 11:01 | 300 |
| 7 | 5 | 131220 | 11:31 | 248 |
| 8 | 1 | 131221 | 7:41 | 199 |
| 8 | 2 | 131221 | 8:21 | 255 |
| 8 | 3 | 131221 | 9:01 | 306 |
| 8 | 4 | 131221 | 9:52 | 276 |
| 8 | 5 | 131221 | 12:31 | 196 |
| 9 | 1 | 131222 | 6:55 | 198 |
| 9 | 2 | 131222 | 7:25 | 200 |
| 9 | 3 | 131222 | 7:50 | 170 |
| 9 | 4 | 131222 | 8:23 | 153 |
| 9 | 5 | 131222 | 8:58 | 111 |
| 9 | 6 | 131222 | 9:33 | 88 |
| 9 | 7 | 131222 | 10:26 | 78 |
| 9 | 8 | 131222 | 10:55 | 73 |
| 10 | 1 | 131223 | 8:10 | 119 |
| 10 | 2 | 131223 | 8:31 | 212 |
| 10 | 3 | 131223 | 8:51 | 221 |
| 10 | 4 | 131223 | 9:45 | 191 |
| 10 | 5 | 131223 | 11:05 | 129 |
| 10 | 6 | 131223 | 12:05 | 102 |

*Fig. 15B*

| Meal # | meal meas # | date | Time | BGM glucose (mg/dL) |
|---|---|---|---|---|
| 11 | 1 | 131223 | 12:05 | 102 |
| 11 | 2 | 131223 | 12:31 | 99 |
| 11 | 3 | 131223 | 13:01 | 152 |
| 11 | 4 | 131223 | 13:51 | 83 |
| 11 | 5 | 131223 | 14:15 | 55 |
| 11 | 6 | 131223 | 14:45 | 50 |
| 12 | 1 | 131223 | 18:36 | 388 |
| 12 | 2 | 131223 | 19:11 | 375 |
| 12 | 3 | 131223 | 19:53 | 254 |
| 12 | 4 | 131223 | 20:15 | 218 |
| 12 | 5 | 131223 | 20:46 | 197 |
| 12 | 6 | 131223 | 21:17 | 149 |
| 12 | 7 | 131223 | 22:12 | 95 |
| 13 | 1 | 131224 | 6:56 | 451 |
| 13 | 2 | 131224 | 7:35 | 393 |
| 13 | 3 | 131224 | 8:34 | 261 |
| 13 | 4 | 131224 | 9:37 | 116 |
| 13 | 5 | 131224 | 10:43 | 66 |
| 14 | 1 | 131224 | 13:25 | 263 |
| 14 | 2 | 131224 | 13:50 | 275 |
| 14 | 3 | 131224 | 14:43 | 227 |
| 14 | 4 | 131224 | 15:22 | 135 |
| 14 | 5 | 131224 | 16:22 | 63 |

*Fig. 15C*

Sigmoid parameter estimates

| | | |
|---|---|---|
| Increasing sigmoid | Cp | 224 |
| Increasing sigmoid | Lp | -0.21 |
| Increasing sigmoid | Sp | 0.48 |
| | | |
| Decreasing sigmoid | Cp | 366 |
| Decreasing sigmoid | Lp | 0.81 |
| Decreasing sigmoid | Sp | 0.67 |

Measured response | Calculated response | Sum err^2 | 1,373

| 1 | 2 | 3 | 4 | 5 | 6 | 7 | 8 | 9 | 10 | 11 |
|---|---|---|---|---|---|---|---|---|---|---|
| Meal | elaps. time (hr) | Meas Gluc. conc (mg/dL) | | Calc Decr. Δ Conc. (mg/dL) | Calc Incr. Δ Conc. (mg/dL) | Net Δ Conc. (mg/dL) | Calc Gluc. conc (mg/dL) | | Err Calc - Meas (mg/dL) | Err^2 (mg/dL)^2 |
| 3 | 0.0 | 205 | | 0 | 0 | 0 | 205 | | 0 | 0 |
| 3 | 0.8 | 286 | | 19 | 98 | 79 | 284 | | -2 | 4 |
| 3 | 1.4 | 301 | | 90 | 197 | 107 | 312 | | 11 | 116 |
| 3 | 2.0 | 283 | | 159 | 218 | 58 | 263 | | -20 | 396 |
| 3 | 4.0 | 146 | | 296 | 224 | -72 | 133 | | -13 | 169 |
| 3 | 6.3 | 60 | | 343 | 224 | -119 | 86 | | 26 | 688 |

Manipulate sigmoid parameters to minimize sum of squared differences between fitted and measured values (col. 8 and 3).

*Fig. 16*

| 1 | 2 | 3 | 4 | 5 | 6 | 7 | 8 | 9 | 10 | 11 | 12 | 13 | 14 | 15 | 16 | 17 | | 19 | 20 | 21 | 22 | 23 |
|---|---|---|---|---|---|---|---|---|---|---|---|---|---|---|---|---|---|---|---|---|---|---|
| Meal | In BG | Incr. Sug | Incr. Sta | Incr. Fat | Incr. Pro | Incr. Carb | Incr. Sug | Incr. Sta | Incr. Fat | Incr. Pro | Incr. Carb. Sens | Incr. Cp | Incr. Lp | Incr. Sp | Incr. Rate 70% | Incr. Rate/Sen | | Dietr. Dose | Dietr. Dose Sens | Dietr. Cp | Dietr. Lp | Dietr. Sp |
| (#) | (mg/dL) | (g) | (g) | (g) | (g) | (g) | (%) | (%) | (%) | (%) | (mg/dL/g) | (mg/dL) | (hr) | (hr) | (mg/dL/hr) | (g/hr) | | (U) | (mg/dL/U) | (mg/dL) | (hr) | (hr) |
| 1 | 311 | 0 | 0 | 0 | 0 | 0 | 0% | 0% | 0% | 0% | 0.0 | 0 | --- | --- | 0 | 0 | | 6.5 | 35.4 | 230 | 0.97 | 0.84 |
| 2 | 112 | 35 | 25 | 20 | 14 | 60 | 37% | 27% | 21% | 15% | 2.1 | 126 | -0.04 | 0.44 | 86 | 41 | | 4.0 | 29.8 | 119 | 0.82 | 0.94 |
| 3 | 205 | 55 | 34 | 38 | 29 | 90 | 36% | 22% | 24% | 18% | 2.8 | 246 | -0.08 | 0.73 | 133 | 48 | | 13.0 | 38.4 | 499 | 1.24 | 0.78 |
| 4 | 254 | 10 | 22 | 29 | 25 | 33 | 12% | 27% | 33% | 29% | 2.9 | 96 | -0.97 | 0.56 | 139 | 48 | | 9.0 | 32.6 | 293 | 0.58 | 0.91 |
| 5 | 179 | 43 | 19 | 0 | 20 | 62 | 39% | 17% | 26% | 18% | 3.0 | 185 | 0.12 | 0.34 | 124 | 42 | | 11.0 | 27.0 | 297 | 1.20 | 1.08 |
| 6 | 55 | 46 | 6 | 28 | 4 | 52 | 82% | 11% | 0% | 7% | 3.0 | 158 | -1.00 | 0.48 | 269 | 88 | | 0.0 | 0.0 | 0 | --- | --- |
| 7 | 289 | 37 | 30 | 20 | 18 | 67 | 33% | 27% | 25% | 18% | 2.9 | 198 | 0.25 | 0.54 | 87 | 30 | | 12.0 | 29.4 | 353 | 1.16 | 0.86 |
| 8 | 199 | 35 | 27 | 20 | 14 | 62 | 37% | 28% | 20% | 15% | 3.0 | 187 | -0.25 | 0.51 | 145 | 48 | | 8.0 | 31.0 | 248 | 0.98 | 0.80 |
| 9 | 198 | 8 | 30 | 51 | 38 | 38 | 6% | 24% | 40% | 30% | 2.9 | 108 | -0.03 | 0.73 | 56 | 19 | | 9.5 | 26.6 | 253 | 0.37 | 0.77 |
| 10 | 119 | 39 | 7 | 0 | 4 | 46 | 79% | 14% | 0% | 7% | 2.6 | 120 | -1.59 | 0.69 | 303 | 115 | | 7.0 | 32.0 | 224 | 1.10 | 0.83 |
| 11 | 102 | 22 | 4 | 0 | 2 | 26 | 79% | 14% | 0% | 7% | 3.6 | 93 | -0.45 | 0.24 | 141 | 39 | | 6.0 | 34.4 | 206 | 0.53 | 0.68 |
| 12 | 388 | 0 | 0 | 0 | 0 | 0 | 0% | 0% | 0% | 0% | 0.0 | 0 | --- | --- | 0 | 0 | | 13.0 | 31.6 | 411 | 0.77 | 0.93 |
| 13 | 451 | 0 | 0 | 0 | 0 | 0 | 0% | 0% | 0% | 0% | 0.0 | 0 | --- | --- | 0 | 0 | | 15.0 | 35.4 | 531 | 0.75 | 0.90 |
| 14 | 263 | 14 | 10 | 0 | 1 | 24 | 56% | 40% | 0% | 4% | 2.8 | 67 | -0.70 | 0.43 | 90 | 32 | | 13.0 | 36.0 | 468 | 0.90 | 0.89 |

*Fig. 17*

Parameter Estimates (sigmoid) for meals 16, 22, 34, and 39

| | 1 | 2 | 3 | 4 | 5 |
|---|---|---|---|---|---|
| | | Incr. | Incr. | Decr. | Decr. |
| meal | | Lp | Sp | Lp | Sp |
| 16 | | 1.03 | 1.82 | 1.86 | 2.29 |
| 22 | | 0.49 | 1.61 | 2.76 | 2.48 |
| 34 | | 0.78 | 1.73 | 2.39 | 2.38 |
| 39 | | 0.79 | 1.76 | 2.64 | 2.40 |

Regression coefficients for factors

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Factor | int. | gSu | $gSu^2$ | gSt | $gSt^2$ | gFa | $gFa^2$ | gPr | $gPr^2$ | dose | $dose^2$ | su/ssf | $(su/ssf)^2$ | st/ssf | $(st/ssf)^2$ | car/do | $(car/do)^2$ |
| Param. | | | | | | | | | | | | | | | | | | |
| Incr. Lp | 0.5 | 2.E-03 | 4.E-05 | 2.E-03 | 2.E-03 | 7.E-05 | 1.E-03 | 5.E-05 | 2.E-03 | 5.E-05 | 6.E-03 | 3.E-04 | 4.E-02 | 2.E-02 | -3.E-01 | -5.E-01 | -3.E-04 | -1.E-04 |
| Incr. Sp | 1.6 | 2.E-03 | 9.E-05 | 2.E-03 | 5.E-05 | 1.E-03 | 1.E-03 | 4.E-03 | 4.E-05 | 4.E-03 | 2.E-04 | 3.E-02 | 2.E-02 | -2.E-01 | -4.E-01 | -2.E-04 | -1.E-04 |
| Decr. Lp | 2.1 | 5.E-03 | 8.E-05 | 5.E-03 | 1.E-04 | 3.E-03 | 1.E-04 | 4.E-03 | 1.E-04 | 1.E-02 | 7.E-04 | 8.E-02 | 5.E-02 | -6.E-01 | -1.E+00 | -6.E-04 | -3.E-04 |
| Decr. Sp | 2.5 | -2.E-03 | -1.E-05 | -2.E-03 | -4.E-05 | -9.E-04 | -3.E-05 | -4.E-03 | -1.E-05 | -4.E-03 | -2.E-04 | -2.E-02 | -1.E-02 | 2.E-01 | 4.E-01 | 2.E-04 | 8.E-05 |

Factor values for meals 16, 22, 34, and 39

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| meal | gSu | $gSu^2$ | gSt | $gSt^2$ | gFa | $gFa^2$ | gPr | $gPr^2$ | dose | $dose^2$ | su/ssf | $(su/ssf)^2$ | st/ssf | $(st/ssf)^2$ | car/do | $(car/do)^2$ |
| 16 | 35 | 1225 | 51 | 2601 | 11 | 121 | 18 | 324 | 9 | 81 | 0.36 | 0.13 | 0.53 | 0.28 | 10.8 | 116 |
| 22 | 12 | 144 | 0 | 0 | 8 | 64 | 8 | 64 | 3 | 9 | 0.60 | 0.36 | 0.00 | 0.00 | 6.7 | 44 |
| 34 | 35 | 1225 | 27 | 729 | 20 | 400 | 14 | 196 | 6 | 36 | 0.43 | 0.18 | 0.33 | 0.11 | 13.7 | 187 |
| 39 | 35 | 1225 | 27 | 729 | 20 | 400 | 14 | 196 | 11 | 121 | 0.43 | 0.18 | 0.33 | 0.11 | 7.5 | 56 |

*Fig. 21*

HUMAN METABOLIC CONDITION MANAGEMENT

RELATED APPLICATIONS

This application is a continuation of U.S. patent application Ser. No. 16/701,401, filed Dec. 19, 2019, which is a continuation of U.S. patent application Ser. No. 15/518,834, filed Apr. 13, 2017, now U.S. Pat. No. 10,529,454, which is a U.S. National Stage Filing under 35 U.S.C. 371 from International Application No. PCT/US2015/055658, filed Oct. 15, 2015, which claims the benefit of priority to U.S. Provisional Application Ser. No. 62/065,146, filed Oct. 17, 2014, the content of which applications are hereby incorporated by reference in their entirety.

BACKGROUND

Metabolism is the process the body uses to get or make energy from the food that has been ingested. A metabolic disorder occurs when abnormal chemical reactions in the body disrupt this process. When this happens, the body may have too much of some substances or too little of other substances needed to remain healthy. A person can develop a metabolic disorder when some organs, such as the liver or pancreas, become diseased or do not function normally. Diabetes is an example of a metabolic disorder.

Diabetes is a group of metabolic diseases in which there are high blood sugar levels over a prolonged period. Symptoms of high blood sugar include frequent urination, increased thirst, and increased hunger. If left untreated, diabetes can cause many complications. Acute complications include diabetic ketoacidosis and nonketotic hyperosmolar coma. Serious long-term complications include cardiovascular disease, stroke, chronic kidney failure, foot ulcers, and damage to the eyes. Diabetes is due to either the pancreas not producing enough insulin or the cells of the body not responding properly to the insulin produced. There are three main types of diabetes:

Type 1 diabetes results from the pancreas's failure to produce insulin. The cause is unknown. Type 2 diabetes begins with insulin resistance, a condition in which cells fail to respond properly to insulin. As the disease progresses a lack of insulin may also develop. The primary cause is excessive body weight and not enough exercise. Gestational diabetes is the third main form and occurs when pregnant women without a previous history of diabetes develop high blood sugar levels.

SUMMARY

Systems and methods for extracting patterns from data for predicting metabolic responses and suggesting a behavior may include receiving, at a computing device comprising a processor, temporal data including information regarding metabolite readings; generating, by the computing device, at least one pattern based on metabolite levels extracted from the temporal data and a variety of factors including medication, food, and activity; formulating, by the computing device, a model for predicting a metabolic response; and storing the model on a data storage device. Based on the model and features disclosed herein, a behavior may be suggested to maintain a metabolic state within a desired range.

DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 13 shows an example food and nutrition log;

FIG. 14 shows an example summary of a food and nutrition log with information from medication and glucose logs;

FIGS. 15A-15C show an example glucose log;

FIG. 16 shows example data and parameters used in fitting a sigmoid form to the example data;

FIG. 17 shows an example of summary sigmoid parameters and statistics for fitting temporal data with sigmoid forms;

FIG. 21 shows a metabolic coefficient model of a person and example factor data, used to estimate parameters for predicting this person's glycemic response.

Corresponding reference characters indicate corresponding parts throughout the several views. The exemplifications set out herein illustrate exemplary embodiments of the invention, and such exemplifications are not to be construed as limiting the scope of the invention any manner.

DETAILED DESCRIPTION

Figure 1:
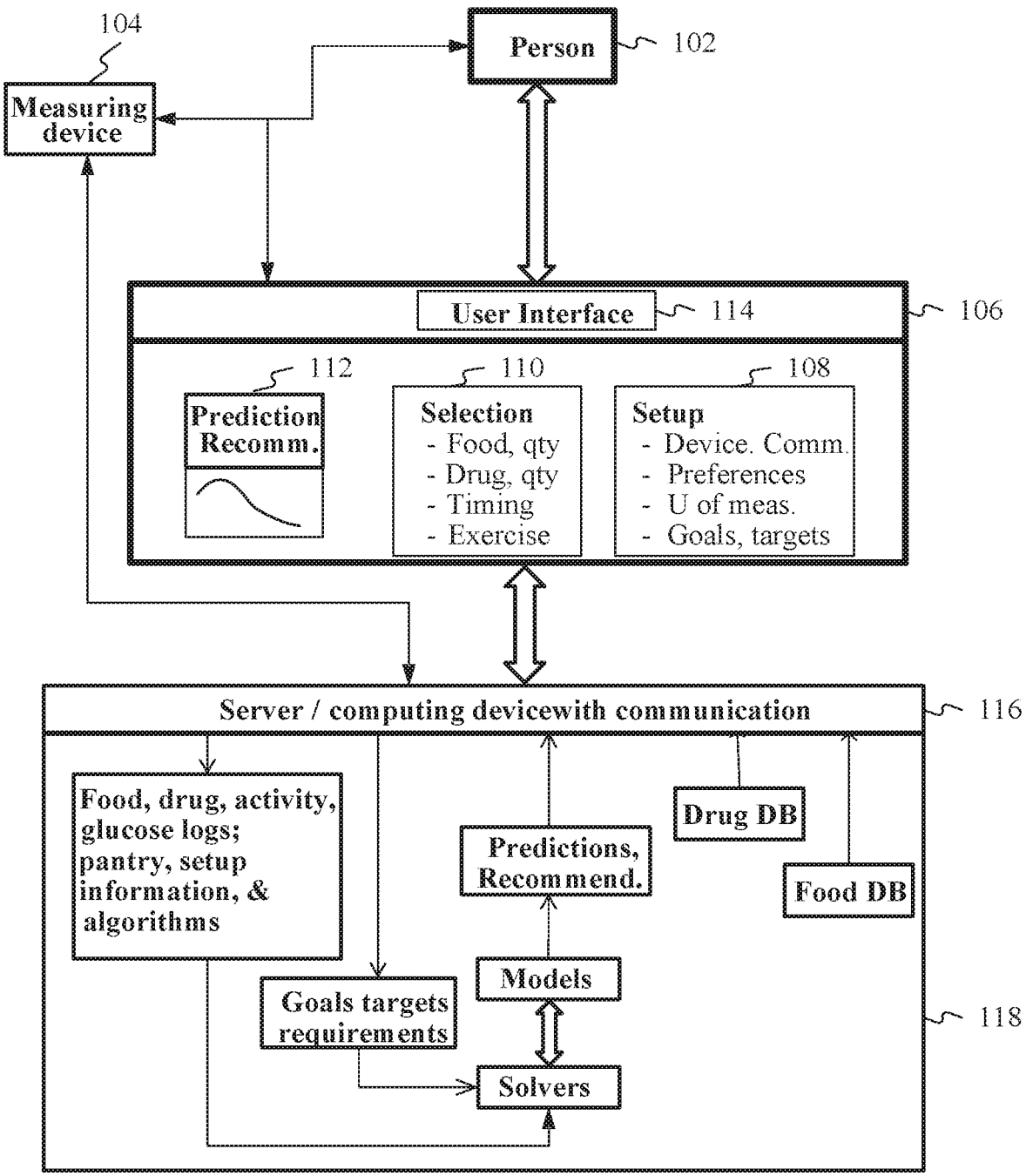
FIG. 1 shows an example schematic of an example system for metabolic management.

The following detailed description refers to the accompanying drawings. Wherever possible, the same reference numbers are used in the drawings and the following description to refer to the same or similar elements. While embodiments and examples are described, modifications, adaptations, and other implementations are possible. For example, substitutions, additions, or modifications may be made to the elements and stages illustrated in the drawings, and the systems and methods described herein may be modified by substituting, reordering, or adding stages to the disclosed methods or elements to the discloses systems. Accordingly, the following detailed description does not limit the disclosure. Instead, the proper scope of any invention disclosed herein is defined by the appended claims.

Many human conditions may be managed by the use of one or more medications that may produce a desired effect when a metabolite is above, below, or within a desired range. Achieving a desired range may be complicated by multiple factors that may influence metabolization, may act simultaneously and at different or varying rates and times. Non-limiting examples of such factors include food, activity, hormones, age, sex, weight, time, stress, disease state, secondary conditions, and others. These may amplify, diminish, delay, affect the rate of action or may otherwise influence a person's metabolism such as glycemic response, increasing the complexity of managing a metabolic condition. Medications used in managing a metabolic condition can include, but are not limited to, insulin, exenatide, liraglutide, pramlintide, metformin, sulfonylureas, meglitinides, thiazolidinediones, DPP-4 inhibitors, GLP-1 receptor agonists, SGLT2 inhibitors, etc.

Central to managing a metabolic condition may be an individual and how his or her body may respond to a multitude of factors that may influence his or her metabolism.

Diabetes is a prevalent metabolic condition manifest by abnormally high or abnormally low levels of the metabolite glucose. Managing diabetes is often complex, multifaceted, and not intuitive. People with diabetes may rely upon conflicted ambiguous experiences, qualitative and quantitative knowledge about relationships between food, medication, activity, sate, and other facets of metabolism that may affect glucose levels.

Diabetes management methods can include, but are not limited to, combinations of formulas, calculations, measuring devices, information from measuring devices, therapeutic devices, medication(s), diet, activity, information logs, means of computing and communicating.

Carbohydrate counting is used interchangeably with carbohydrate to insulin ratio and can be used to estimate dose quantity for the carbohydrate quantity contained in a meal or food. Carbohydrate counting is based upon a sensitivity ratio of carbohydrate to insulin and is specific to an individual. After food and medication are fully metabolized, glucose levels may generally be near an initial pre meal level. However, for an individual, carbohydrates metabolize at different rates, and rates that are different than most medications, and may be influenced by the presence of other macro nutrients, thus resulting in potentially large variations in glycemic responses, attendant difficulty, and consequences.

Insulin sensitivity factor (ISF) uses the rule of 1500 or the rule of 1800 to estimate a person's sensitivity to insulin. An ISF value of 20 means that a person's blood glucose will be reduced by 20 mg/dL per unit of insulin. ISF may be estimated from a lookup table, based on the type of meal time insulin a person uses, and the person's total daily insulin intake; basal and meal time insulin.

Figure 3:
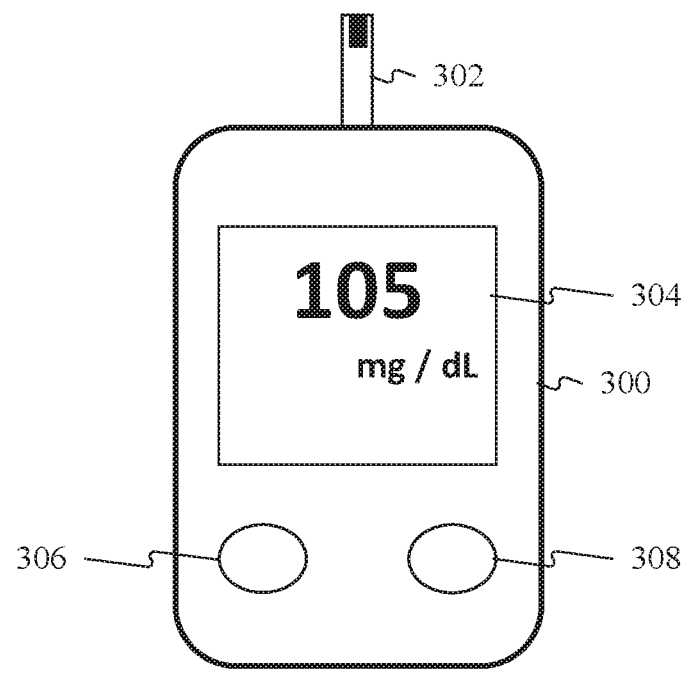
FIG. 3 shows an example of a blood glucose meter.

Blood glucose meters (BGM), such as shown in FIG. 3, may measure a user's blood glucose level at a point in time. This information often may be used in conjunction with carbohydrate counting when making decisions regarding food and dose quantities. BGMs commonly have logging features for activity, food, and medication. Absent glucose information such as that provided by BGMs, the likelihood of diabetic complications or severe hypoglycemic events requiring medical assistance may increase significantly. In 2010, the Center for Disease Control (CDC) reported that nearly 500,000 people with diabetes in the US visited emergency rooms for hypo or hyperglycemia.

Continuous glucose meters (CGM) may be wearable wireless devices that may take frequent measurements and may provide information in various forms including, but not limited to, a graph that may indicate glucose levels over time, the current glucose concentration, recent glucose history, trajectory, and wireless signals. This may enable users to anticipate excursions from a desired range, or respond to imminent hypoglycemic events, such as shown in the schematic shown in FIG. 4A. CGMs commonly have logging features for activity, food, and medication.

Figure 4A:
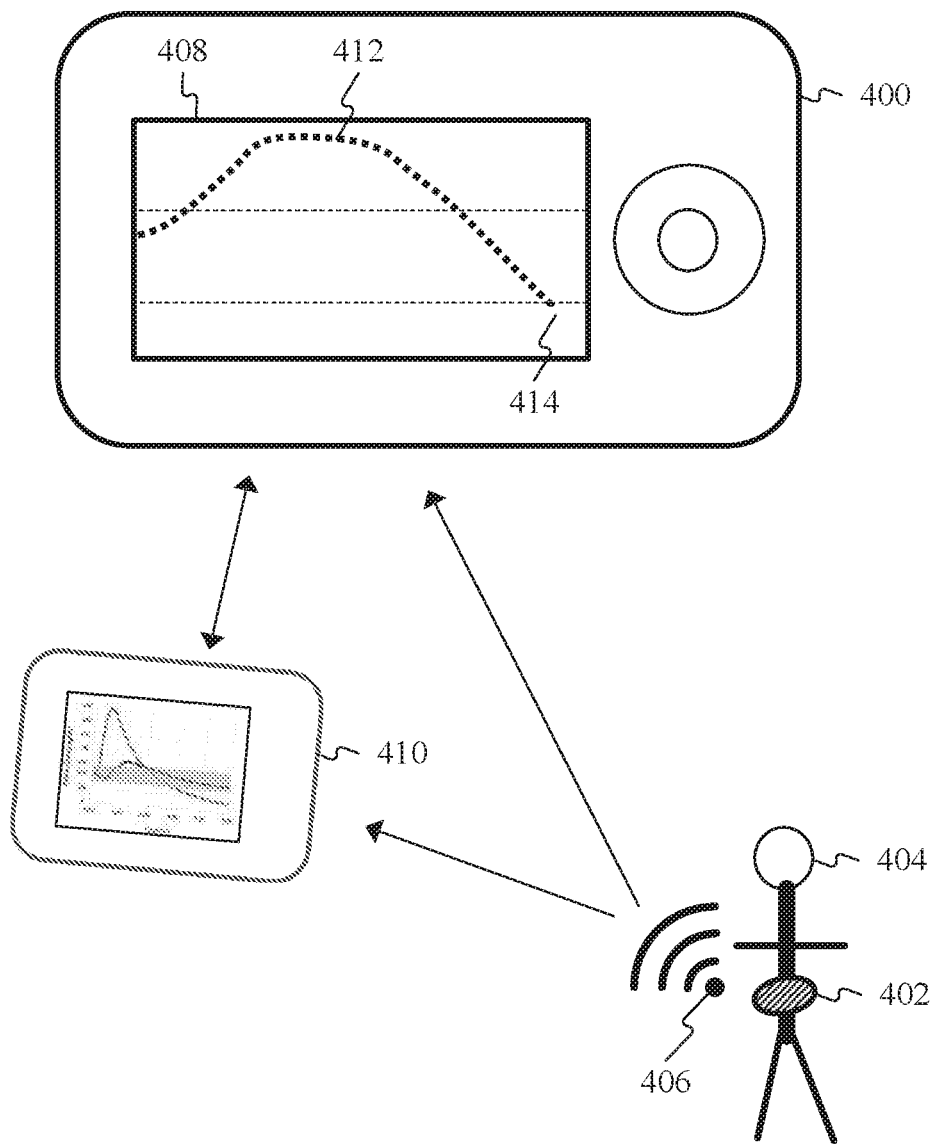
FIG. 4A shows an example of a continuous glucose meter.
Figure 4B:
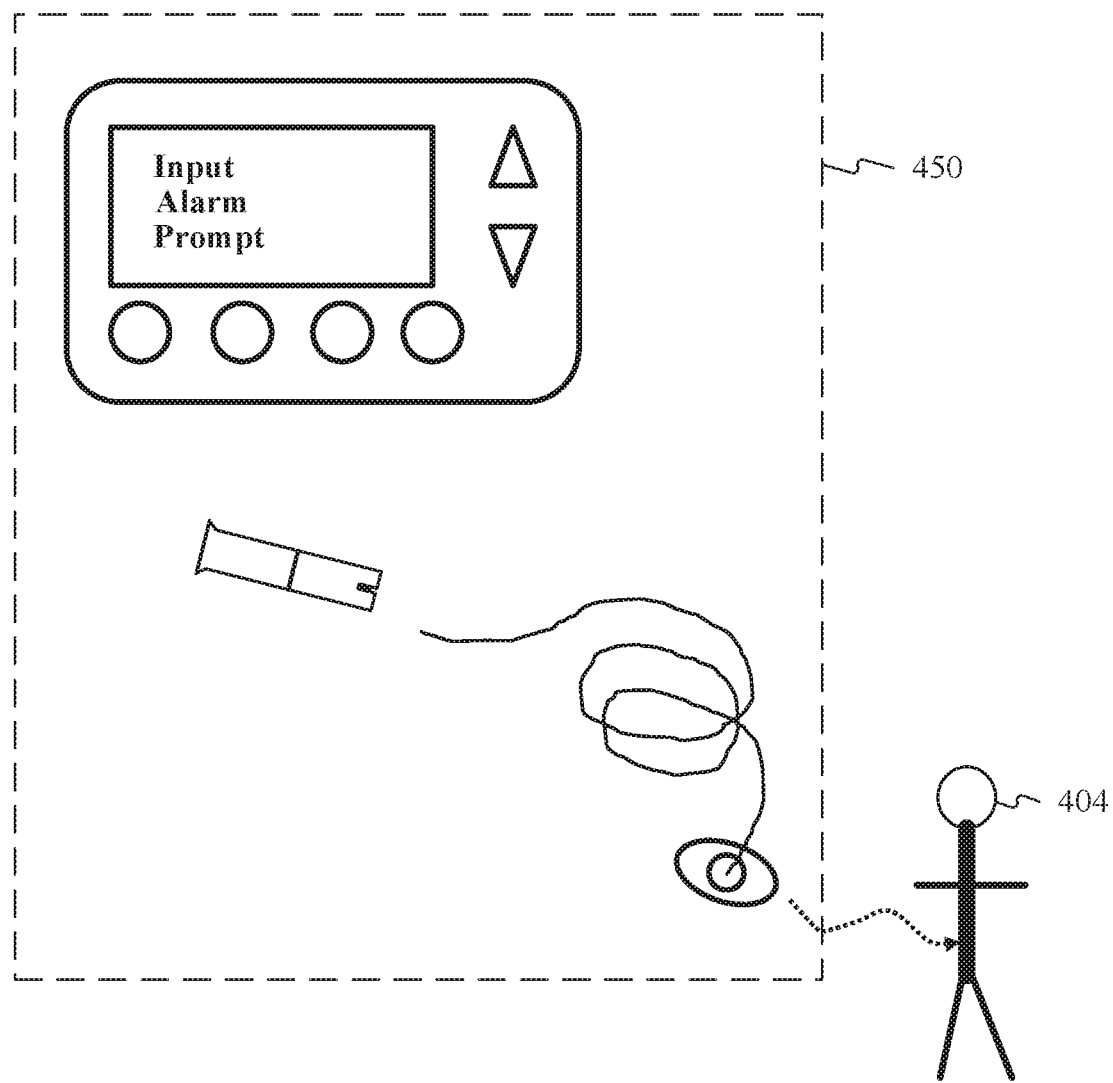
FIG. 4B shows an example of an infusion pump.

FIG. 4B shows a user 404 and an infusion pump system 450 which may consist of a pump with communication means, a medication reservoir, and cannula by which medication can be delivered to a person. Infusion pump system 450, as schematically shown in FIG. 4B, may be wearable devices that may be used to infuse medication in precise quantities in a manner which may generally help improve metabolite regulation. To initiate an insulin infusion for a meal, the wearer may communicate to the pump the quantity of medication that may be desired or the quantity of carbohydrate that may be ingested. The quantity of infused insulin may be based on a carbohydrate counting method, which may include adjustments. Pumps may also infuse at programmed rates, times, or quantities, such as described and shown. An insulin pump, CGM, and smartphone may be combined to create a device that regulates glucose in both increasing and decreasing concentrations.

The effects of medication composition, quantity, and timing on a metabolite such as glucose can vary substantially as shown and described with respects to FIGS. 5, 6, 7A, 7B, 8B, 8C, 9, 10A, 10B, and 12A-12F.

The effects of food composition, quantity, and timing on a metabolite such as glucose can vary substantially as shown and described with respect to FIGS. 5, 6, 7A, 7B, 8A, 8C, 9, 10A, 10B, and 12A-12F.

Figure 11:
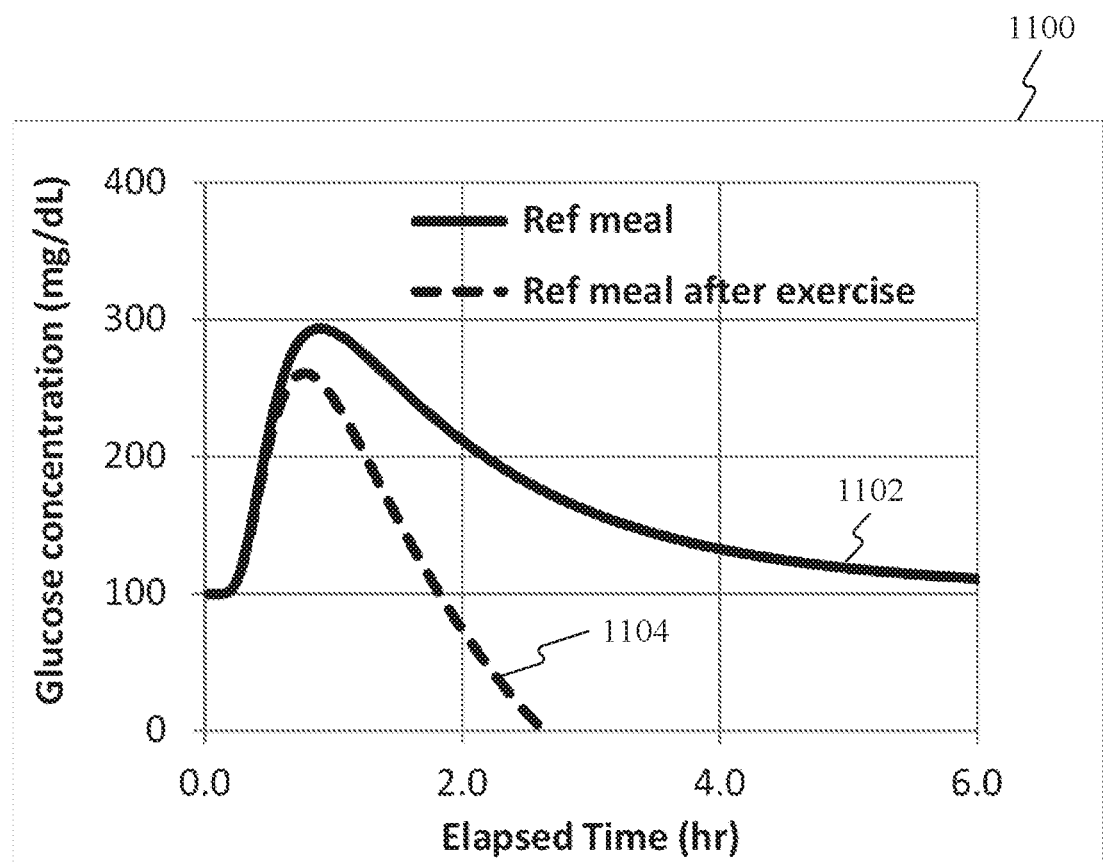
FIG. 11 shows a plot showing how exercise may influence blood glucose response.

The effects of activity on a metabolite such as glucose, such as shown and described with respect to FIG. 11, may affect a person's sensitivity to medication, and thus may require less medication for a desired effect. For diabetes management the carbohydrate to insulin ratio may be a mercurial device whose numerical value may be affected by activity and time, which may further complicate challenges related to managing metabolic conditions like diabetes.

Insulin on board (JOB) is a method that can be used to estimate how many units of insulin are not yet metabolized and are "on board" in a person's body at a point in time after administering a dose. This method may use a formula based on a constant decay rate (e.g., 30% reduction/hour) to estimate JOB.

Type 2 Diabetes (T2D) is a form of diabetes where insulin metabolism is impaired. One or more drugs are often used to treat T2D, each having metabolic characteristics that may be specific to an individual. In addition, more than 30% of people with T2D may use insulin and/or oral medication like those described herein. Type 2 Diabetes drug classes function by: stimulating the pancreas to produce and release more insulin, inhibiting the production and release of glucose from the liver, blocking the action of stomach enzymes that break down carbohydrates, and improving the sensitivity of cells to insulin. Additionally, Type 2 Diabetes may sometimes be managed through combinations of medications, weight loss, weight control, diet, and exercise.

The International Diabetes Federation estimates that more than 380 million people in the world have diabetes, in the United States more than 25 million people. The American Diabetes Association in 2012 estimated the economic cost of diabetes in the United States at about $250 billion/year. Of the 25+ million people with diabetes in the United States, there are more than 21,000 deaths per year from hypoglycemia, and nearly 500,000 emergency room visits resulting from hyperglycemia or hypoglycemia. Additionally, severe complications and death also result from chronic hyperglycemia associated with diabetes.

In 1993, the National Institute of Health's (NIH) Diabetes Control and Complications Trial (DCCT) demonstrated many significant health benefits from reducing chronically elevated glucose concentrations through frequent glucose measurements and frequent administration of insulin. Since 1993 there has been increased effort to manage diabetes by reducing average glucose levels as expressed in a person's hemoglobin A1C value. The DCCT used hemoglobin A1C as an index to measure a person's level of control. A1C may be used as a proxy for time weighted average glucose level, which is typically <6% for a person without diabetes. Hemoglobin A1C measures the fraction of hemoglobin which has glucose bound to it.

The NIH's DCCT study established substantial health benefits from lowering average glucose levels in people with diabetes. The incidence diabetes complications affecting the heart, eyes, nerves, and kidney were reduced between 42 and 76%. However, the incidence of hypoglycemia increased 300% A method to reduce the mean and range, or variation of glycemic responses is needed to mitigate hazards associated with frequent or severe hypoglycemia that often accompany lower average glucose levels. Disclosed are systems and methods to create predictive metabolic models that enable improved management of metabolic conditions.

During use, temporal data comprised of metabolite measurements and logs for factors that may influence metabolites of interest can be recorded. Non-limiting examples of temporal data include, a glucose log, a food/nutrition log, a medication log, and an activity log. The glucose log may include a date and time of glucose measurements. FIGS. 15A-15C, discussed below, shows an example glucose log. A food/nutrition log may include a food description, quantity of food, and a start time for ingesting food. Food identifiers sufficient to estimate nutritional content are desirable, or a means of obtaining nutritional information, and may also include a person identifier. FIG. 13, discussed below, shows an example food/nutrition log. A medication log may include an identification of medications taken, dosage of the medications, and a time the medications were administered. An activity log may include a start time, intensity, and duration of activities.

Data from capture, monitoring, regulating, or logging devices can also be used to provide information used to create predictive models. For example, glucose meters may have electronic logs for glucose readings, carbohydrate intake, insulin dosage, and activities. Additionally, other means of obtaining or logging information may also be suitable, such as, but not limited to, software applications, digital devices, image capture, image analysis, barcode reading, wireless sensors etc.

Logged data may be arranged for analysis, data may be fitted to forms that reasonably represent the data, and preferably whose fit parameters have physical meaning. For example, metabolic responses to various foods, medication doses, and activities may be represented by one or more sigmoid forms, each which may be defined by three or more parameters, such as scale, location, and shape as shown and discussed with regard to FIG. 6. An effect form that may be useful is the sigmoid form, although an effect may take other forms or shapes. Response may equal the summation of effects and interactions, as shown in Eq. 1, which may take different forms. An example of an effect form that may be useful is the Cumulative Lognormal Probability Function (CPF) generally defined by three parameters. Other effect forms may also be useful such as sigmoids and other forms and shapes.

The scale parameter, $C_p$, is a multiplier that represents the total effect of a factor. In other words, the scale parameter represents the capacity of a factor to effect a change when fully metabolized. The unit of measure of the scale parameter are those used to measure the metabolite of interest. The range of $C_p$ varies by metabolite, unit of measure, and individual person. For glucose the absolute value of $C_p$ may range from 0 to 50,000 mg/dL.

The location parameter, $L_p$, of sigmoid forms is a central feature and may be estimated by the median or log mean normal of a data set. It is a point about which data is distributed in a generally symmetrical manner. The location parameter may represent the time required to reach 50% (or log mean) of the full scale value of an effect. Large location parameter values correspond to effects that require more time to manifest themselves. Small location parameter values correspond to effects that require less time to manifest themselves. $L_p$ may be measured in units of time or units appropriate to a metabolite model. The range of $L_p$ values varies by metabolite, person, and unit of measure. The range may vary from 0 to 10,000 hours. For factors affecting glucose $L_p$ may range from 0 to 5,000 hours, for foods 0 to 20 hours, and for medications from 0 to 5,000 hours. These given values are expressed in real values rather than a logarithmic scale.

The shape parameter, $S_p$, indicates how an effect is distributed over time relative to the location parameter, $L_p$. Large shape parameter values correspond to effects that are distributed over larger spans of time. Small shape parameter values correspond to effects that are distributed over small spans of time about $L_p$. $S_p$ may be measured in units of time or units appropriate to a metabolite model. Values of $S_p$ may vary by metabolite, person, and other factors. Generally, $S_p$ values may range from 0.001 to 10 hours for the metabolite glucose. $S_p$ values for food may range from 0.01 to 5, and for anti-diabetes medications $S_p$ values may range from 0.01 to 10.

Metabolic events may be modeled by combining multiple sigmoid forms to show an overall result of the metabolic events. Each event may have a corresponding set of parameters. For example, ingesting food may be modeled by an increasing sigmoid form and an insulin dose may be modeled by a decreasing sigmoid form. Thus, the glycemic response may be represented by a combination of increasing and decreasing sigmoid forms. Depending on the relative influence of each, the overall result could predict a future hypoglycemic or hyperglycemic state.

One approach to creating a predictive model may include assuming of a response form, the geometric or mathematical form of the metabolic response, followed by fitting the form to the measured response data. For example, one or more sigmoid forms may be useful representations of temporal metabolic responses, including but not limited to glucose. To estimate parameters of a sigmoid form, solvers may be used to minimize the sum of the squared differences between fitted values and measured values of the response. Creating models can also include relating parameters to medications, food, activity, etc. that can have an effect on a metabolite. Alternative methods such as Monte Carlo simulation, maximum likelihood, and others may also be used to estimate form parameters. In addition, multiple runs may be used to generate representative estimates of form parameters.

Metabolic events can be coupled. Coupled metabolic events are those with effects that overlap in time. For example, if a medication which is largely metabolized within 5 hours is administered now, and another dose is administered 1.5 hours from now then these two dose events are likely coupled and form parameters for each may be estimated through fitting. For responses of a sigmoid form, the location parameter and the shape parameter may be useful to determine if effects are coupled.

After fitting metabolic responses to a representative form, such as sigmoid forms, parameter estimates from fitting may be combined with factor data and analyzed for useful relationships. For example, after fitting glycemic responses to sigmoid forms, relationships between factors such as insulin quantity or carbohydrate quantity may relate to the sigmoid form scale parameter $C_p$. A large variety of methods may be used to generate predictive relationships between factors and parameters. The methods include, but are not limited to methods that use or combine, statistical, visual, mathematical, analytics, predictive analytics, data mining, machine learning, neural networks, deep learning, dimensional reduction, principal component, latent variable, covariant based methods, categorical methods, and more. Such methods may also be used to relate factors to responses without fitting to an intermediate form.

A variety of methods may be used to relate form parameters to factors used in 208 models. For example, if the increasing sigmoid parameter for location, $L_p$, relates well to 1/% carbohydrate, then this relationship may be used to predict the $L_p$ parameter for future meals of this person. Factors may be transformed, combined, and/or combinations of these may be used to develop useful relationships with form parameters. Similarly, form parameters may also be transformed, combined, and/or combinations of these may be used to develop useful relationships with factors. Non-limiting examples of combinations and transforms are presented in FIG. 18A-18C and FIG. 19A-19C. A variety of statistical methods may also be used to relate form parameters and factors. Non-limiting examples include methods utilized in machine learning, data mining, analytics, predictive analytics, and deep learning methods.

One such combination and transformation that may generate useful relational patterns is rate, for example, by Eqs. 2A-2F. For example, for a sigmoid form for an average rate of metabolism may be estimated by combining percent of metabolism completed (e.g. complement of insulin on board), scale parameter, location parameter, and shape parameter. This may be repeated for a number of meals. If a useful pattern between grams of carbohydrate and rate exists, the pattern may be expressed as an equation which may be used to estimate parameters, such as $C_p$, $L_p$, and $S_p$, used to make temporal predictions. Statistical methods for pattern generation, detection, or utilization may also be utilized.

$$\text{Avg. Rate}_1 = \frac{Cp(\%_2 - \%_1)}{(lognorm^{-1}(\%_2, Lp, Sp) - lognormal^{-1}(\%_1, Lp, Sp))} \quad \text{Eq. 2A}$$

$$\text{Avg. Normalized Rate} = \frac{(\%_2 - \%_1)}{(lognorm^{-1}(\%_2, Lp, Sp) - lognormal^{-1}(\%_2, Lp, Sp))} \quad \text{Eq. 2B}$$

-continued $$\frac{\text{Avg Rate}_1}{\text{Sensitivity}} = \frac{\frac{Cp(\%_2 - \%_1)}{(lognorm^{-1}(\%_2, Lp, Sp) - lognormal^{-1}(\%_1, Lp, Sp))}}{\frac{C_p}{\text{quantity}}} \quad \text{Eq. 2C}$$

$$\text{Time to \%} = lognorm^{-1}(\% \text{ complete}, Lp, Sp) \quad \text{Eq. 2D}$$

$$[\text{Parameter Est}] = ([\text{Regression Coeff}] \times [\text{Factor value}]) \quad \text{Eq. 2E}$$

$$\text{Avg. Rate}_2 = \frac{Cp}{(lognorm^{-1}(\%_2, Lp, Sp) - lognormal^{-1}(\%_1, Lp, Sp))} \quad \text{Eq. 2F}$$

The units of Eq. 2A are:

$$\left[\frac{\text{mg/dL}}{\text{hr}}\right]$$

The units of Eq. 2B are:

$$\left[\frac{\%}{\text{hr}}\right]$$

The units of Eq. 2C are:

$$\left[\frac{\frac{\text{mg/dL}}{\text{hr}}}{Sens \text{ Units}}\right]$$

The units of Eq. 2D are:

[hr]

The units of Eq. 2F are:

$$\left[\frac{\text{mg/dL}}{\text{hr}}\right]$$

An average rate may be expressed as a ratio of a change in effect to a corresponding or appropriate time. The unit of measure may be scale units of measure per unit time; which typically may be units of concentration per hour.

A normalized rate is a useful pattern that may also be realized using a normalized rate transform. For example, the average rate divided by the scale parameter measured in units of percent change per hour may be a useful rate.

An instantaneous rate may be the first derivative of the sigmoid form. The instantaneous rate can vary dramatically over the time required for an effect to be fully metabolized. Generally, the average rate may be useful and computationally simpler to calculate than the instantaneous rate.

Data may include identifiers like a person's name, ID number, date, time, meal number, etc. Food data may include identifiers such as SKU, brand, descriptors, quantity, nutritional data, and ingestion start date and time. A number of electronic devices may facilitate data capture, such as calorie counting apps, fitness apps, image analysis, barcode readers, etc. Medication data may include an identifier of the medication (brand name or generic name), concentration, dosage, quantity, date and time of administration, if infused, location of infusion site, etc. Activity data may include a start date and time, intensity, and duration. Intensity may use a subjective scale. Information from monitoring devices such as smart watches, health monitors, FITBIT®, and other wearable devices may also be incorporated and utilized to record data. Identifiers may be used to obtain detailed information such as composition which may then be used for analysis. Glucose measurements may be obtained from glucose measurement logs, manual, electronic, and/or digital, and may include measurement method, device identifier, measurement location, glucose concentration, and date and time.

For estimating sigmoid parameters, data may be arranged for analysis and include identifiers, and measured responses. From this elapsed time of metabolic events, elapsed time since last activity (e.g., exercise), change in metabolite value may be calculated. As discussed herein, sigmoid fit parameters may be estimated by minimizing the sum of squared errors between fitted response and the measured response. Minimization of the sum of squared errors may utilize simulation methods such as non-linear solvers, maximum likelihood, Monte Carlo, or other statistical, mathematical, or algorithmic methods.

As discussed herein, coupled effects occur when effects overlap in time. For example, if a medication is fully metabolized in 5 hours and a dose is administered at time equals zero followed by a second dose at time equals plus 2 hours, then the effects of the two doses are coupled and may be accounted for in the fitting or modeling. Eq. 1 accommodates this circumstance. Overlapping doses of medication such as insulin may result in coupling which may occur frequently in diabetes management and is referred to as insulin stacking. Stacking of effects may apply to other effects such as food. For example a person with diabetes may stack their carbohydrate intake over time rather than a single sitting. Such coupling and stacking effects may occur not only with insulin, but also with one or a combination of food, medication, activity, and the like.

The scale parameter of a sigmoid form may be expressed as the product of quantity and sensitivity; quantity times sensitivity. For glucose, sensitivity to medication may be estimated from the ratio of fitted scale parameter $C_p$ to medication dose, and sensitivity to carbohydrates as the ratio of fitted scale parameter $C_p$ to carbohydrate intake. In diabetes management insulin sensitivity is utilized by health care professionals, people who self-medicate, insulin pumps, pump users, and users of carbohydrate counting methods. Carbohydrate sensitivity may also be useful in glucose management.

In diabetes management, insulin sensitivity is often estimated by formulas, such as the rule of 1500, the rule of 1800, trial and error, intuition, or other non-data based methods. As indicated, sensitivity may have a mercurial nature, given its role in decision making, frequent use, and its relative importance in decision making, using the systems and methods disclosed herein for empirical estimates of sensitivity may enhance glycemic control.

Additionally, the systems and methods disclosed herein may be dynamic and revised periodically as data is added to the system's logs. This flexibility enables improved predictions and can help compensate for circumstances that may be transient in nature such as disease state, pregnancy, puberty, life changes that effect hormones, change in medications, change in methods of medicating, and more.

The systems and methods disclosed herein may include measurement devices, portable computing devices, remote computing devices, logging devices, and a communication means, which may be used to provide predictions and/or acquire data in real time. In addition, the system and methods disclosed herein may be used to supplement the utility of devices such as CGMs, insulin pumps, or other metabolic management devices. The systems and methods disclosed herein may also be used with other portable and remote computing devices such as smart phones to provide predictions in addition to or in conjunction with measured values.

For example, the systems and methods disclosed herein may be used with infusion pumps. Infusion pumps with predictive capabilities may be used to deliver medication in a manner that minimizes excursions from target response values, ranges, or profiles. For instance, the infusion pumps may be able to regulate actions by estimating combinations of quantity, rate, frequency, duration, and/or timing of medication to infuse.

Response maps may be generated from models and varying values of sigmoid parameters for effects that increase and decrease metabolite values. Thus, the systems and methods disclosed herein allow for a desired response to be specified and actions that may be used to achieve the desired response.

FIG. 1 shows an example schematic of an example system 100 for metabolic management. As shown in FIG. 1, a user 102 may utilize at least one glucose sensor 104 to measure blood glucose levels. The user 102 and the glucose sensor 104 may interact with a portable computing device 106. The portable computing device 106 may include setup information 108, selection information 110, and predictions/recommendations 112. The setup information 108 may include user preferences, units of measurement, goals, targets, etc. The selection information 110 may include foods eaten or to be eaten (including quantity), medications taken or to be taken (including dosages), exercise schedule, and timing for meals and medications. The predictions/recommendations 112 may include predicted blood glucose levels and recommendations regarding timing for exercise, meals, and medications. The user may interact with portable computing device 106 via a user interface 114.

The portable computing device 106 may interact with a server or other remote computing device 116. The remote computing device 116 may receive and store information 118. The information 118 may include, but is not limited to, food and drug information, glucose logs, pantry items, goals, predictions, models, etc. The information 118 may be initially stored on the remote computing device 116, may be sent to the remote computing device 116 from portable computing device 106, and calculated and stored by the remote computing device 116. The portable computing device 116 may also be a portable communications device.

Figure 2:
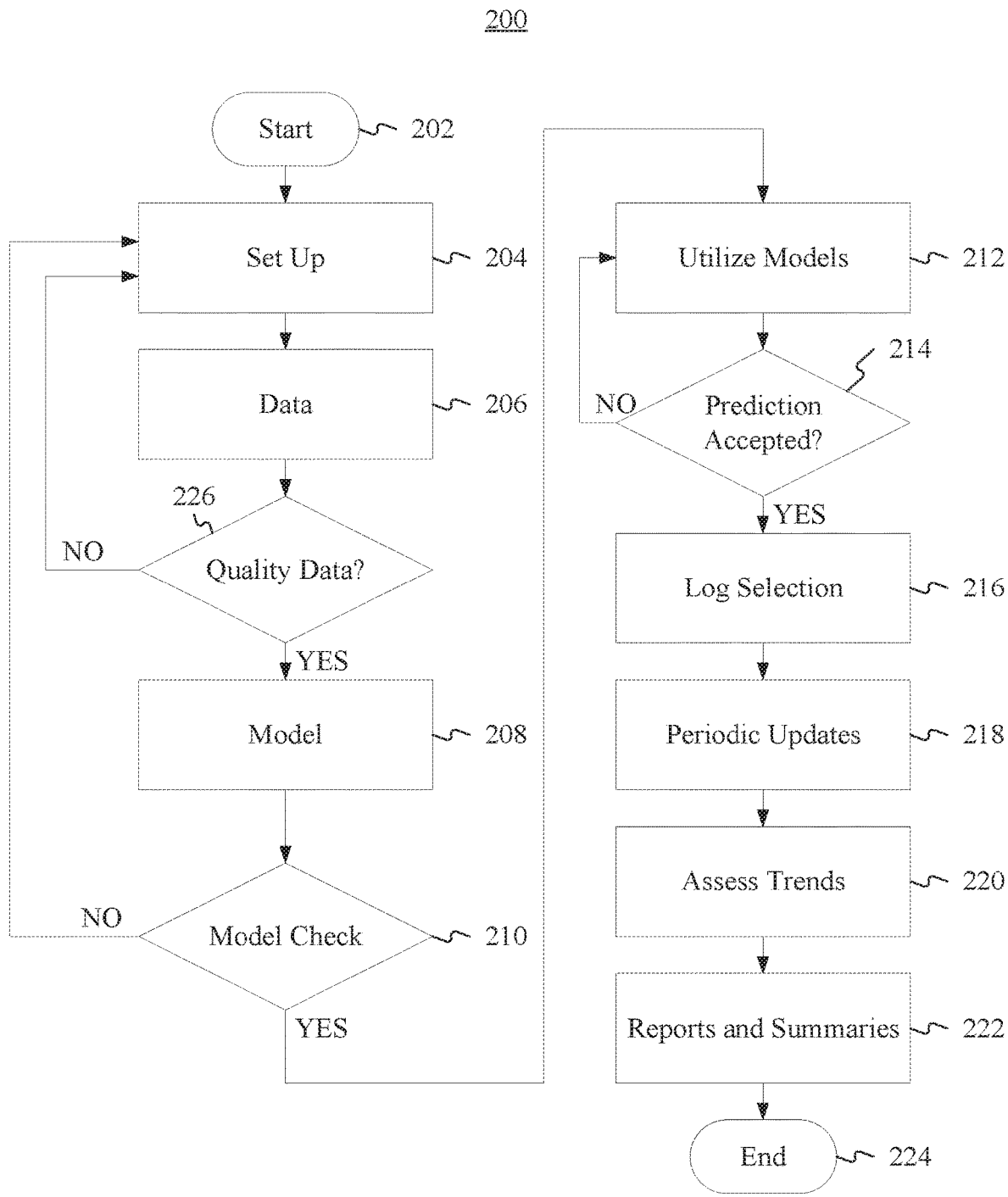
FIG. 2 shows an example flow chart for creating metabolic models.

FIG. 2 shows an example flowchart for a method 200 for creating an example predictive metabolic model. The method 200 may be implemented via the portable computing device 106, the remote computing device 116, or a combination of both. The method 200 may start at stage 202 and proceed to stage 204 where setup data may be entered. A non-limiting example of entering setup data may include a setup process that may include entering information such as user ID, goals, medications taken, carbohydrate to insulin ratio, food preferences, restrictions, body parameters such as, but not limited to, weight, heights, sex, a pantry inventory, frequently eaten foods, and more. The setup process may also include the portable computing device 106 retrieving the data from a database.

From stage 204 the method 200 may proceed to stage 206 where data such as log data may enter the system or be accessed. For example, data from food logs, exercise logs, continuous glucose meter files, etc. may enter the system at 206 or later be accessed from 206. For instance, upon first use, the portable computing device 106 may create logs. During use, the portable computing device 106 may access logs previously created and add new log information as it is received.

From stage 206, the method 200 may proceed to decision block 226 where a determination can be made as to if the data is quality data. In other words, at decision block 226 determination can be made as to if enough data is present for statically significant results, is there missing data, coupled data, etc. The quality check may also include pre-analysis such as sorting data, calculating statistics such as mean, median, standard deviation, etc.

From decision block 226 the method 200 may proceed to stage 208 where data may be analyzed to create models. For example, for one meal, temporal glycemic data, changes in glucose from the start of the meal may be fitted to sigmoid forms to estimate sigmoid parameters. This is repeated for the log information. Form parameters may then be examined for relationships to food, medication, activity, and/or other factors. Estimating form parameters such as $C_p$, $L_p$, and $S_p$ from relationships to factors such as food and or medication may be used to create predictive models. During the modeling process, various approaches may be taken. For example, as discussed herein parameter—factor relationships may be used, machine learning algorithms may be applied to parameter factor data, and machine learning algorithms may be applied to raw data to create models.

From stage 208 the method 200 may proceed to decision block 210 where the models may be checked. For example, this may include testing the model by predicting glycemic responses to meals that were logged but not used to create a model, then comparing the predicted values to the measured values to assess the model. Criteria for checking the models may include, by are not limited to, mean absolute mean error, goodness of fit parameter $R^2$, etc. This may also be applied to meals used to create a model. If models can be categorized, predictions from a model may be compared to predictions of other models of the same or similar category to assess a new or updated model. For biological systems $R^2$ values greater than 60% are considered typical. $R^2$ criteria values greater than 80% are preferred, and more preferably greater than 95%.

If the model check is not successful, the method may proceed to stage 204 where more data or other information may be requested. If the model check is successful, the method 200 may proceed to stage 212 where a prediction can be supplied to the user 102. For example, based on the model, a prediction that the user's 102 blood glucose may drop below an acceptable level within the next hour. Based on the prediction, a food may be suggested to the user to be eaten within 30 to 40 minutes. Based on a user's 102 predicted glycemic response other suggestions or recommendations may be provided to the user 102. For example, a recommendation may include taking medication, exercising, refraining from eating, etc.

In making the recommendation, a behavior pattern may be received from a user as described herein. The behavior pattern can be one or more activities the user 102 may perform. For example, the user 102 may input that the user 102 is going to ingest food and administer a medication within 30 minutes of ingesting the food. Using this behavior pattern, a recommendation may be provided. For example, based on the food to be ingested, the recommendation may be to cut the medication dosage in half or take the medication from between 10 and 15 minutes prior to ingesting the food.

In addition, other factors can be used to make the recommendation. For example, as disclosed herein various restriction, or constraints, can be imposed on the recommendation. The constraints can be associated with foods and medications the user may be allergic to or medications that could have harmful reaction if taken with another medication. Furthermore, as for recommending foods, a user's dietary likes and dislikes and weight control can be considered. For example, a user may be trying to lose weight or control carbohydrate intake. Thus, when selecting a recommendation, a high calorie high carbohydrate food may be avoided.

Moreover, restrictions on metabolite levels can be used as a constraint on recommendations. For example, a user, under a doctor's care, may want to limit glucose levels to within a certain range (e.g., 80 to 130 mg/dL). As a result, given the user's current glucose level, the solver calculating predicted response levels and selecting recommendations may avoid or be prevented from selecting a recommendation that would cause a response that would put the user's glucose level outside the range. For instance, if the user's current glucose reading is 90 mg/dL and the user is planning to exercise (e.g., run 5 miles), the system, in anticipation of the activity that is likely to cause a drop in the glucose level may recommend the user to eat before the run to counter the drop in glucose level. However, since the user wants to limit his or her glucose range to between, for example, 80 to 130 mg/dL, the system may recommend the user eat a piece of fruit instead of a piece of candy.

From stage 212 the method 200 may proceed to decision block 214, where a determination can be made as to whether the user 102 accepted the recommendation. If the user 102 did not accept the recommendation the method 200 may proceed to stage 212 where another recommendation may be supplied. If the user 102 accepted the recommendation, the method 200 may proceed to stage 216 where the recommendation can be logged. For example, the user may indicate acceptance of the recommendation by pressing a button on portable computing device 106. Upon accepting the recommendation, portable computing device 106 may log that the user is going to eat a banana within the next 20 to 30 minutes. In addition, accepting the recommendation may be noted by the user entering into portable computing device 106 that the user ate or performed some other activity listed in the recommendation within the allotted time period. The activity entered by the user 102 can be logged as well.

From stage 216 the method 200 may proceed to stage 218 where models may be revised. As new data accumulates in the logs 116, it may be combined with previous log data to revise and improve models as described in stage 208. Model updates may be triggered based on user prompt, quantity of accumulated data, age of last model version, prediction accuracy, calendar based triggers, or a variety of other means. For example, modeling as described herein may be applied to accumulated logged data on a monthly basis.

From stage 218 the method 200 may proceed to stage 220 where trends may be monitored and assessed. For example, if prediction errors exhibit a bias that increases with time this may indicate a maladies, a life change such as puberty, or other conditions. This may be followed by a variety of actions such as a prompt to log data more frequently to improve accuracy.

From stage 220 the method 200 may proceed to stage 222 where reports and summaries may be generated. For example, trends in insulin and/or food (carbohydrate) sensitivity may be of value to user and health care providers. Non limiting examples relating to the invention may include a scatter plots of measured versus predicted glucose values may be provided to users to quickly inform them of the models' state; another example report may consist of a plot of $R^2$ versus date.

Reports or summaries may be provided periodically, by user prompts or preferences, system administrators, or other means. For example, weekly, monthly, or quarterly. Access to reports and or summaries may be controlled by a user 102. From stage 222 the method 200 may terminate at termination block 224. While the method 200 has been described with respect to the portable computing device 106, the various stages, may be implemented using remote computing device 116, or a combination of portable computing device 106 and remote computing device 116.

FIG. 3 shows an example blood glucose meter (BGM) 300. A BGM may be used as a method to measure glucose. The method may require lancing a fingertip, drawing a drop of blood, and placing the blood on a reagent strip 302. The reagent strip may be inserted into the BGM 300 which converts reagent signals to glucose concentration. Measurements can be taken as needed, desired, or recommended. The BGM 300 gives a single glucose measurement at a point in time, such as displayed on display 304. The BGM 300, for example by pressing buttons 306 or 308, may transmit stored data such as glucose measurement data, carbohydrate, and activity logs to the portable computing device 106. In addition, BGM 300 may be the portable computing device 106.

FIG. 4A shows a non-limiting example of a continuous glucose meter (CGM) 400. CGM systems may be comprised of a wearable sensor 402 worn by user 404, a transmitter 406 that wirelessly transmits signals to a receiver of the CGM 400. Continuous glucose sensors may be inserted through the skin, implanted, worn without penetrating skin, or measure other signals or indicators that track fluctuations in glucose levels. Continuous glucose sensors can be worn in the abdominal region and can be used for several days to more than a week before needing to be replaced. The receiver can be a portable device with a user interface, such a portable computing device 106. CGM 400 may receive sensor signals and store or display sensor data on display 408. CGM 400 may also communicate with other wireless devices such as a smartphone 410 and instrumentation found in medical facilities. The communication can be via transmission protocols such as, but not limited to, Bluetooth® and Wi-Fi®, or by wire. The display 408 may also show user selectable trigger levels for hyperglycemic 412 and hypoglycemic 414 alarms.

Figure 5:
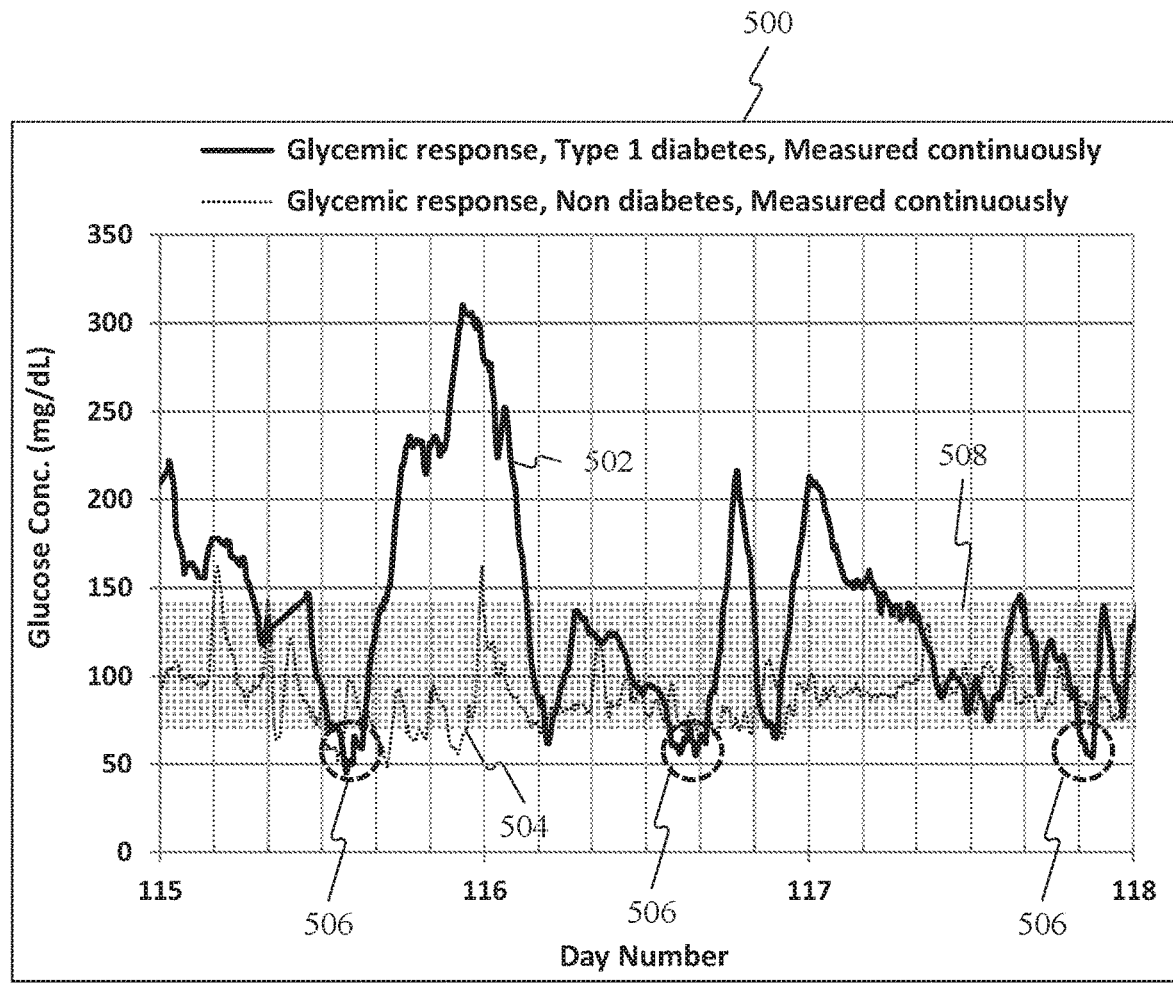
FIG. 5 shows a plot of data from a continuous glucose monitoring.

FIG. 5 shows a plot 500 of 3 days of CGM data from a person with Type 1 Diabetes 502 and a second person without diabetes 504. FIG. 5 illustrates several issues related to managing diabetes. The person with Type 1 Diabetes maintains A1C values near 6.1%, less than 6% is considered normal for people without diabetes. A1C may be thought of as a time weighted 90 day moving average glucose level. Though average glucose values for the person with Type 1 Diabetes are within an acceptable range, daily excursions from normal vary widely. Lowering the average glucose level of a person with diabetes increases the likelihood of hazards associated with severe and or frequent hypoglycemic events 506. The range (indicated by shaded region 508) of glucose for a person without diabetes may be from 80 to 140 mg/dL.

Figure 6A:
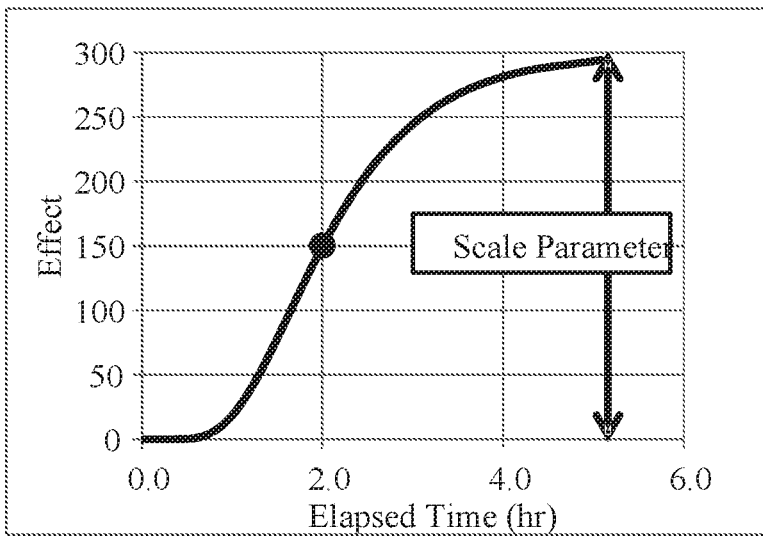
FIGS. 6A-6C show sigmoid forms and parameters for scale, location, and shape.
Figure 6B:
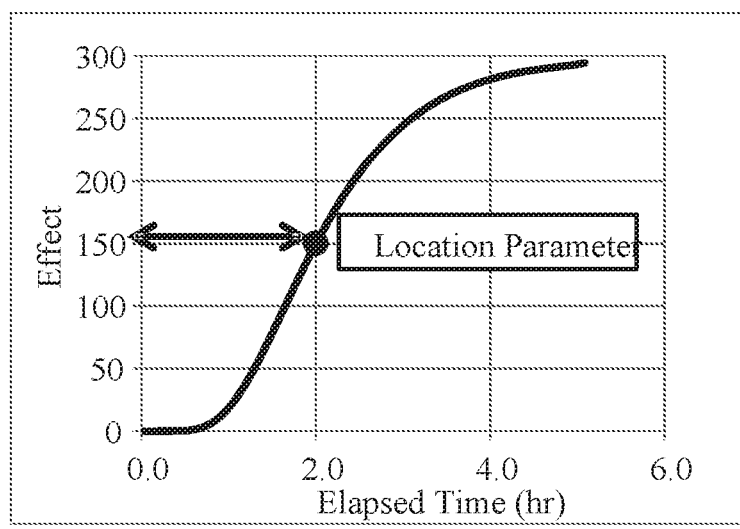
Figure 6C:
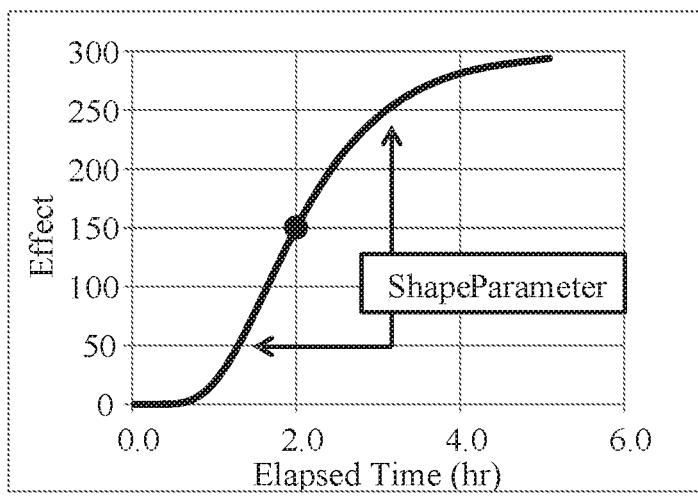

FIGS. 6A-6C show a sigmoid form and parameters for scale, location, and shape. A sigmoid form is one of a plurality of forms that may be fitted to temporal data described above with respect to the method 200. The scale parameter $C_p$ represents the capacity of an effect to influence a response after it is largely metabolized. The location parameter, $L_p$, of sigmoid forms is a central feature and may be estimated by the median or log mean normal of a data set. It is a point about which data is distributed in a generally symmetrical manner. The location parameter may represent the time required to reach 50% (or log mean) of the full scale value of an effect $C_p$. The shape parameter, $S_p$, indicates how an effect is distributed over time relative to the location parameter, $L_p$.

Figure 7A:
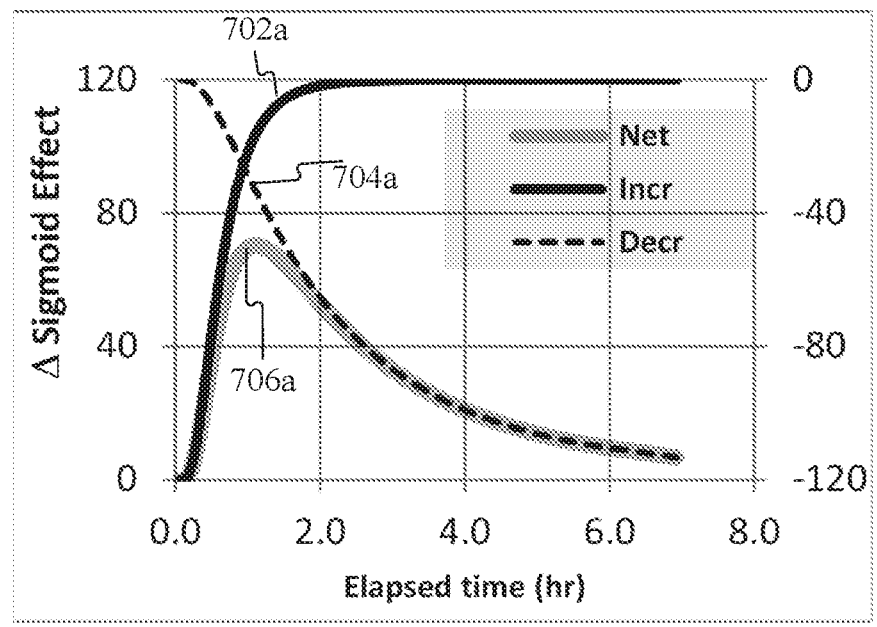
FIGS. 7A and 7B show simulated sigmoid forms.
Figure 7B:
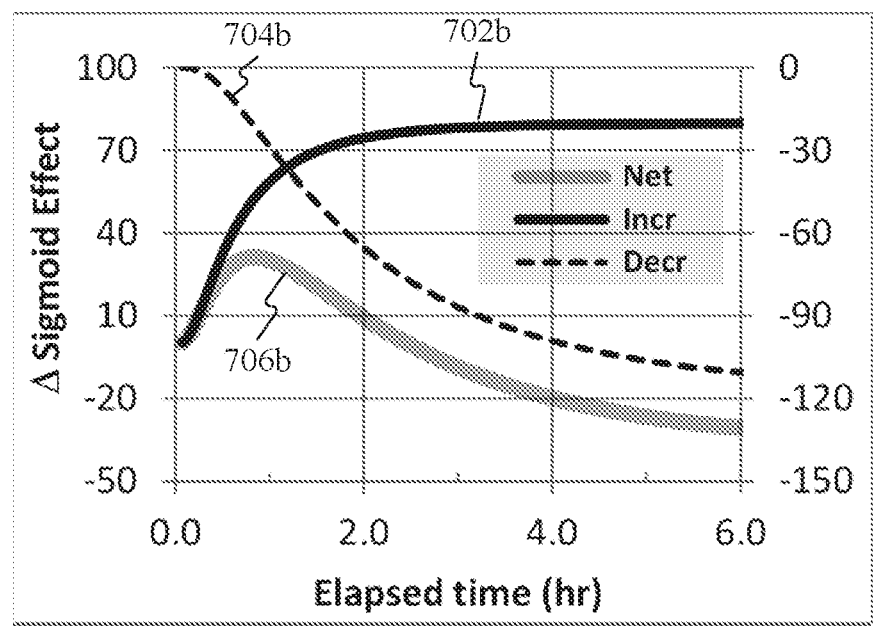

FIGS. 7A and 7B show simulated sigmoid forms for increasing 702, decreasing 704, and summation 706 of the increasing and decreasing sigmoid forms. These two graphs illustrate the influence constituent sigmoid forms can have on the net sigmoid form. As shown in FIG. 7A, the scale parameters, $C_p$, are approximately equal for the increasing and decreasing sigmoid forms. Therefore, after the increasing and decreasing effects are largely metabolized, the end point of the net response approximates its initial value. The location and shape parameters of the increasing and decreasing sigmoid forms differ contributing to the shape of net responses 706a and 706b. In FIG. 7B, the magnitude of the decreasing $C_p$ value is greater than increasing Cp value, therefore after the effects are largely metabolized, the end value of the net response may be lower than the initial value. As shown in FIG. 7B, the scale, location, and shape parameters for the increasing and decreasing sigmoid forms differ.

Figure 8A:
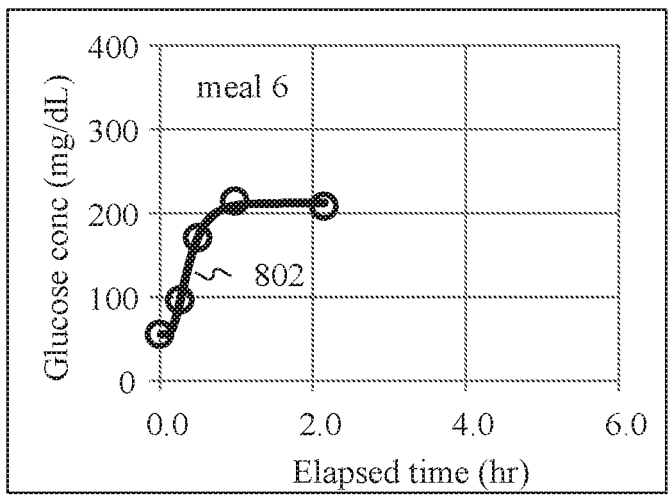
FIGS. 8A-8C show measured and fitted sigmoid forms for various glycemic responses.
Figure 8B:
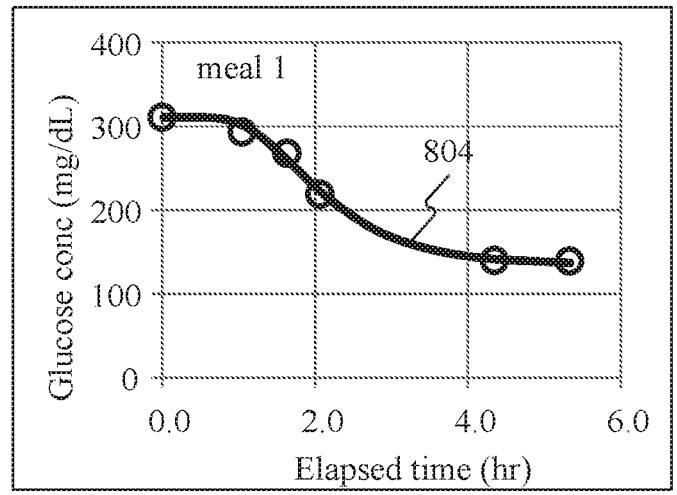
Figure 8C:
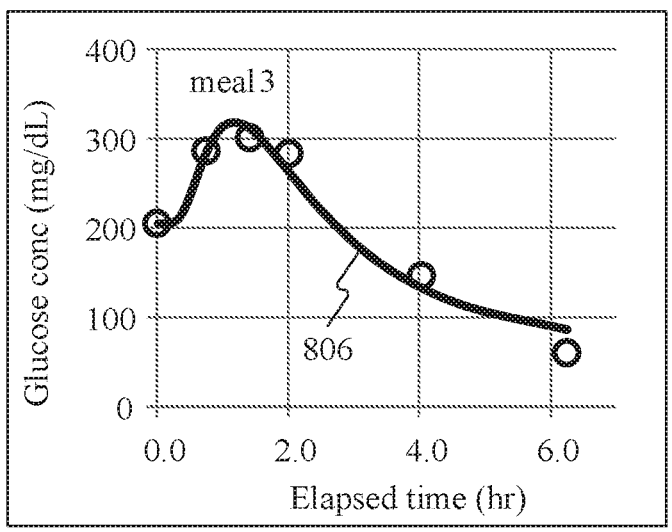

FIGS. 8A-8C show measured data and fitted sigmoid forms for increasing 802, decreasing 804, and summation (net) 806 of increasing and decreasing sigmoid forms. The measured data and fit sigmoid forms illustrate glycemic responses having sigmoidal form for eating (FIG. 8A), receiving insulin (FIG. 8B) and eating and receiving insulin (FIG. 8C). As can be seen by a comparison of FIGS. 8A-8C with FIGS. 7A and 7B, actual results for various glycemic responses can be approximated using sigmoid models.

Figure 9:
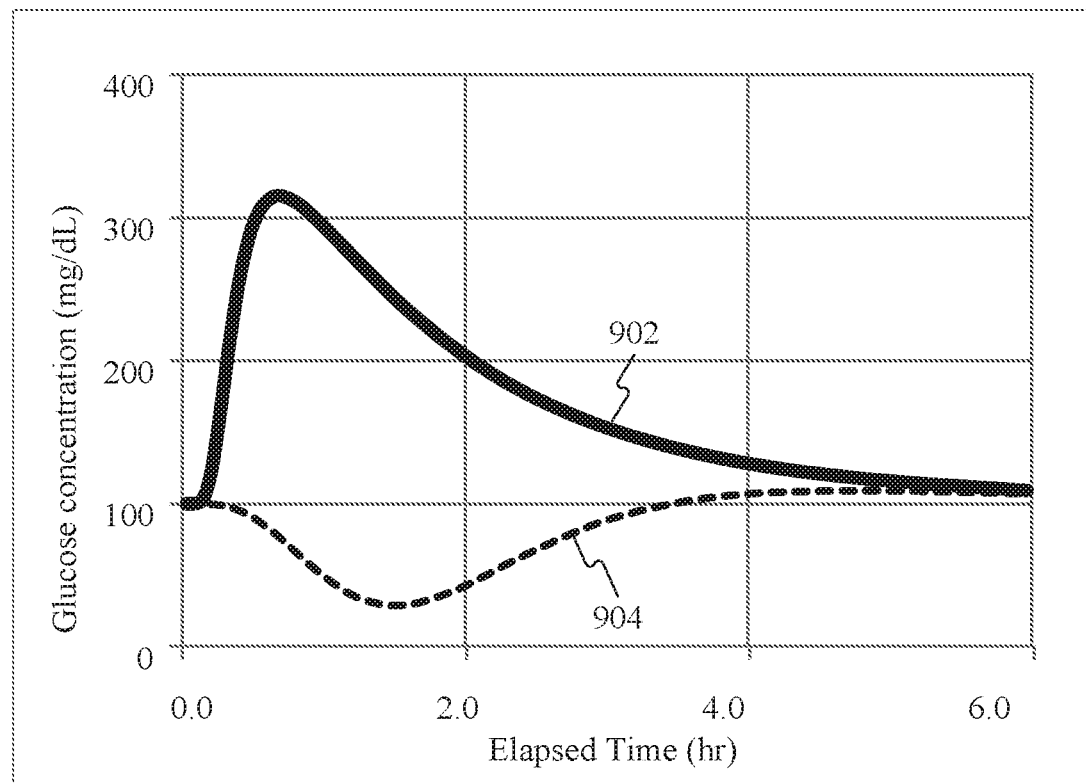
FIG. 9 is a plot showing the influence of changing the location parameter of a sigmoid effect.

FIG. 9 shows the simulated effect of location parameters on net response. The net responses 902 and 904 in FIG. 9 represent two meals composed of food and medication. The sigmoid forms used to represent the increasing and decreasing effects are the same except for the location parameters of the increasing effects. The two net responses are substantially different, to a person with diabetes the net response 902 might correspond to a rapidly metabolized food like orange juice and the net response 904 may correspond to a slowly metabolized food such as pasta. The plot illustrates the influence of sigmoid location parameter on net response, and a potential relationship between metabolic rate and location parameter. Thus, a predictive method that accounts for food composition may be useful for reducing average glucose levels without increasing the hazards of hypoglycemia or hyperglycemia.

Figure 10A:
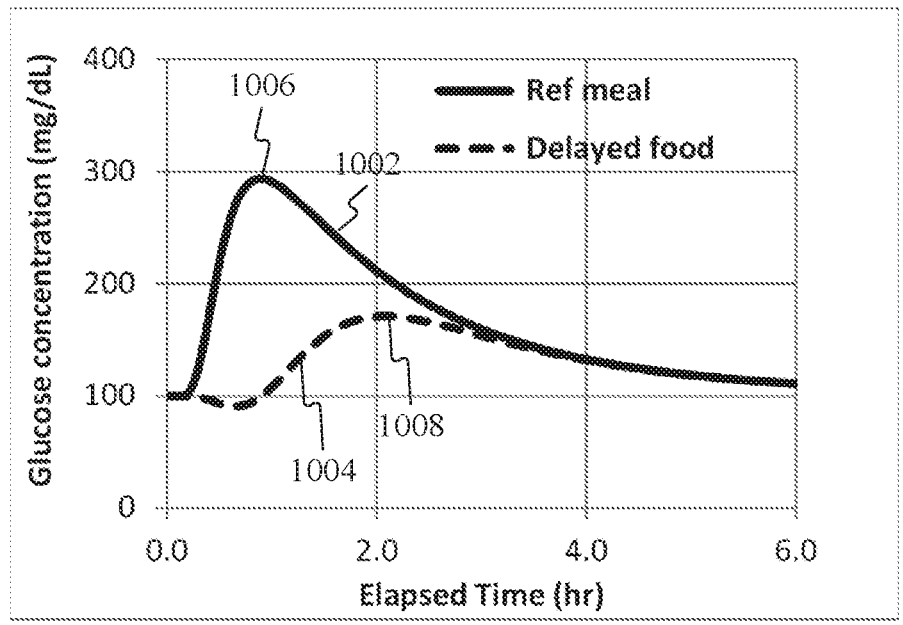
FIGS. 10A and 10B shows the influence of time lag between medication and food, on blood glucose.
Figure 10B:
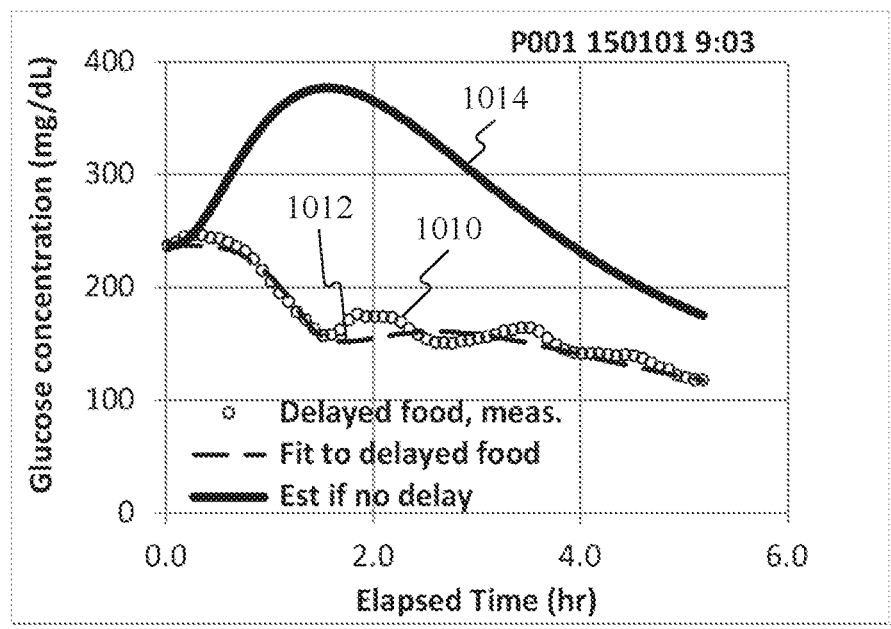

FIGS. 10A and 10B show simulated and measured effect of timing for administering medication, such as insulin, and ingesting food. The two responses in FIG. 10A represent glycemic responses of meals composed of food and medication that are identical except for a time lag between ingesting and receiving medication. For reference meal (1002), there was no time delay between receiving insulin and ingesting food. 1004 is identical to 1002 except food ingestion was delayed after receiving insulin. Variations in timing may be reflected in adjustments to the location parameter $L_p$.

As shown in FIG. 10A, the peak glucose concentration of the meal with delayed food (point 1006) is reduced substantially relative to peak glucose concentration of the reference meal (point 1008). The choice of how long to delay can depend on many simultaneous factors, such as, but not limited to, an individual's metabolism, current glucose level, the food, the amount of food, medications, dosages, and more.

Curve 1010 in FIG. 10B represent a measured glycemic response where the food of an actual (non-simulated) meal was delayed 1.2 hours after receiving insulin. Curve 1012 represents the sum of an increasing and a decreasing sigmoid fitted to the measured data. Curve 1014 shows an estimated response with no food delay calculated by adjusting the location parameter of the fitted increasing sigmoid to estimate the net response if dose and food were received at the same point in time. The similarities between 1002 and 1014; 1008 and 1010-1012 indicate a method that may be internally consistent. As shown in FIGS. 10A and 10B, accounting for timing between food and medication may offer the potential for reducing average glucose levels without the hazards of hypoglycemia or hyperglycemia.

FIG. 11 shows a simulated effect of activity on glycemic response. A first curve 1102 and a second curve 1104 show glycemic responses for meals composed of food and received medication that are identical except for sensitivity to medication for the decreasing sigmoid. 1104 was simulated by adjusting the sensitivity of the decreasing sigmoid of 1102. The simulated net response shows the influence activity on net response that is consistent with experience and literature. Literature also indicates that as an activity event ages, its influence on sensitivity may diminish. As shown in FIG. 11, activities such as exercise may contribute to hypoglycemic events via increased sensitivity to anti-diabetic drugs. Thus, accounting for the effects that may modify a person's sensitivity to anti-diabetic drugs offers the potential for reducing the risk of hazards associated with hypoglycemia by providing information regarding timing and severity of glycemic excursions.

FIGS. 12A-12F show samples of measured glycemic responses (circular points) fitted to sigmoid forms (solid lines). As shown in FIGS. 12A-12F, the shapes of these glycemic responses relate to the fitted sigmoid form parameters, which in turn may relate to factors such as but not limited to medication, food, and or activity.

Figure 12A:
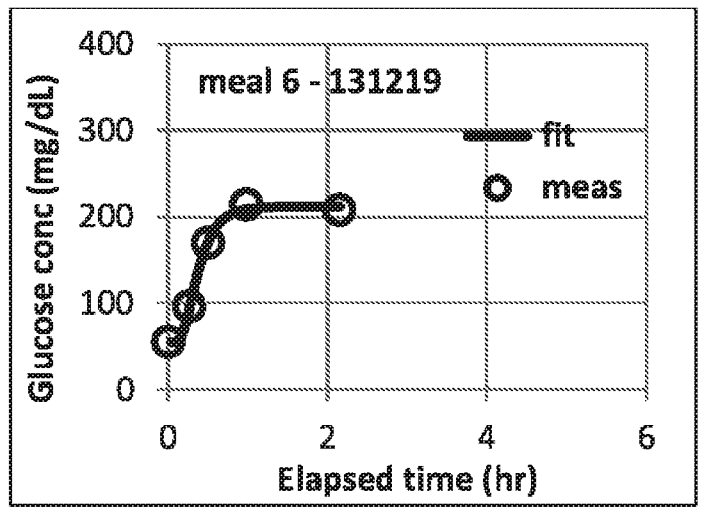
FIGS. 12A-12F show measured glycemic responses and sigmoid forms fitted to the measured responses.
Figure 12B:
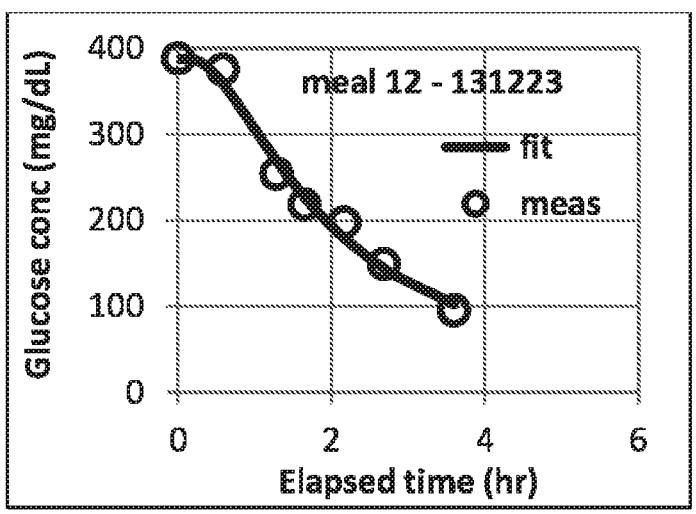

In the FIGS. 12A and 12B only one effect, increasing or decreasing, appears to be active which is consistent with the logs for these meals, FIGS. 13 and 14. Thus illustrating that the increasing and decreasing nature of the measured responses may be reasonably modeled using sigmoid forms.

Figure 12C:
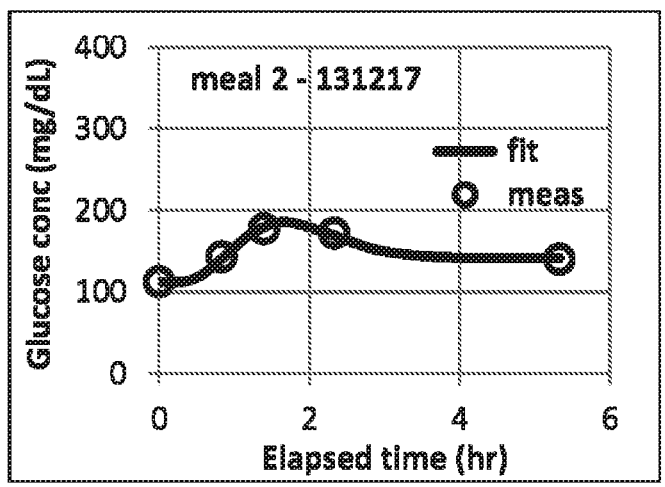
Figure 12D:
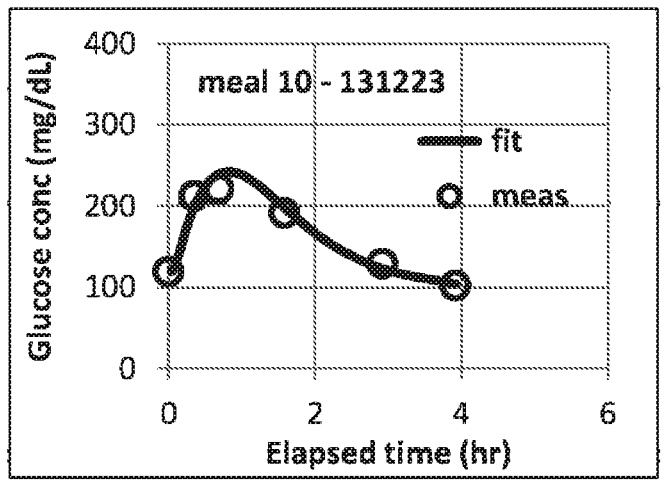

In FIGS. 12C and 12D, the scale parameters of sigmoid forms are nominally equal, as seen in FIG. 17 showing the fitted $C_p$ values. This is evident from the start and end blood glucose levels being similar after food and insulin are largely metabolized. Though the food and insulin quantities were well matched, the paths to similar end points vary. This illustrates the variation of an individual's metabolic response to food and insulin, and how a predictive method may provide utility by anticipating harmful variations in glycemic responses.

Figure 12E:
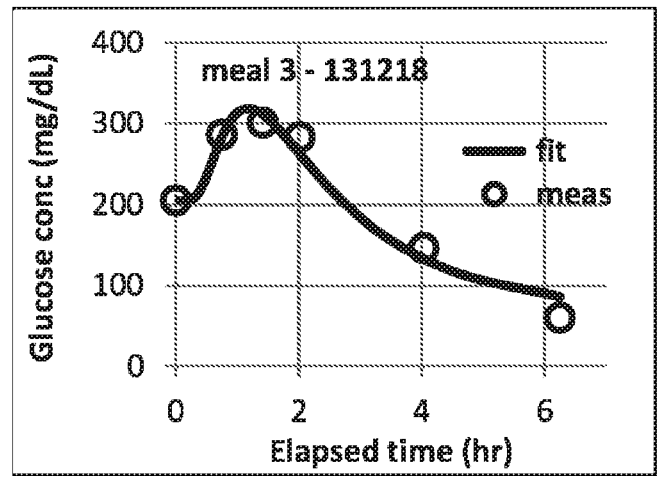
Figure 12F:
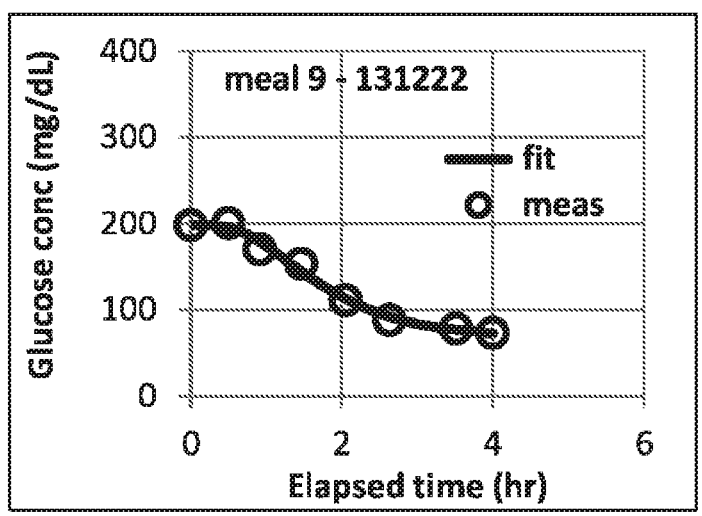

In FIGS. 12E and 12F, the decreasing sigmoid scale parameters are larger than the increasing sigmoid parameters by more than about 100 mg/dL. This indicates that the end blood glucose level concentrations may be lower than the start concentration by about 100 mg/dL. The increasing sigmoid scale parameter of meal 9 is about 150 mg/dL. However, beneficially the glycemic response does not exhibit the characteristic rise after ingesting food as shown in FIGS. 12C, 12D, and 12E.

In FIGS. 12E and 12F, the person's blood glucose levels start off at about 200 mg/dL glucose and both end at about 80 mg/dL. This indicates that the carbohydrate to insulin quantities were similar, yet the glycemic responses are markedly different. The difference may be explained in part by food composition, FIGS. 13 and 14, and how an individual metabolizes food and insulin. Thus, as shown in FIGS. 12A-12F, accounting for composition may offer the potential for reducing average glucose levels without the hazards of hypoglycemia or hyperglycemia.

FIG. 13 shows an example food and nutrition log with date and time stamps not shown.

FIG. 14 shows a summary of food and nutrition log with date and time stamps not shown, combined with elements of medication and glucose logs.

FIGS. 15A-15C shows an example of glucose log.

FIG. 16 shows example data and parameters used in fitting a sigmoid form to the example data. The example data shown in FIG. 16 is fitted to one or more sigmoid forms using least squares and a non-linear solver. The various statistics for the fitting process are shown in FIG. 16.

FIG. 17 shows a summary of sigmoid parameters and statistics from fitting temporal data to sigmoid forms. The data includes sensitivity, and average rate per sensitivity. Data such as this may be used to detect or form patterns, useful relationships, and or additional parameters that can be used to better manage recommendations for controlling glycemic responses.

Figure 18A:
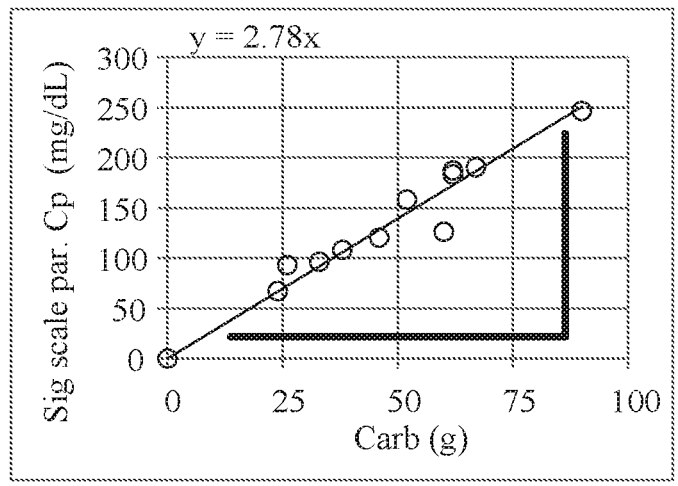
FIGS. 18A-18C show examples of relationships between factors and parameters of sigmoid forms used to create a model of an individual's glycemic response to food.
Figure 18B:
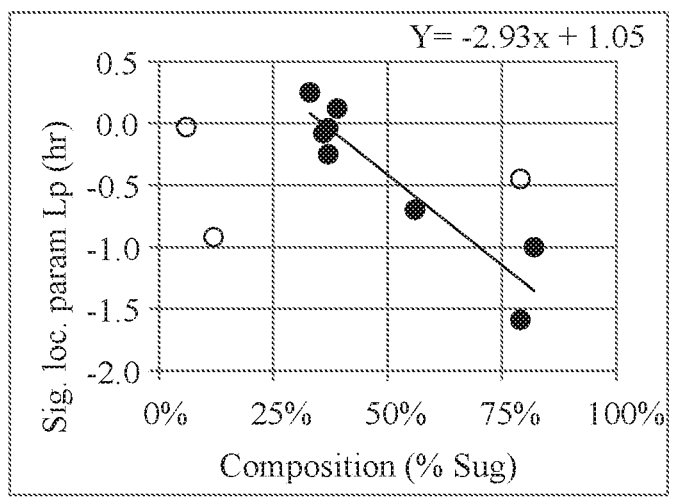
Figure 18C:
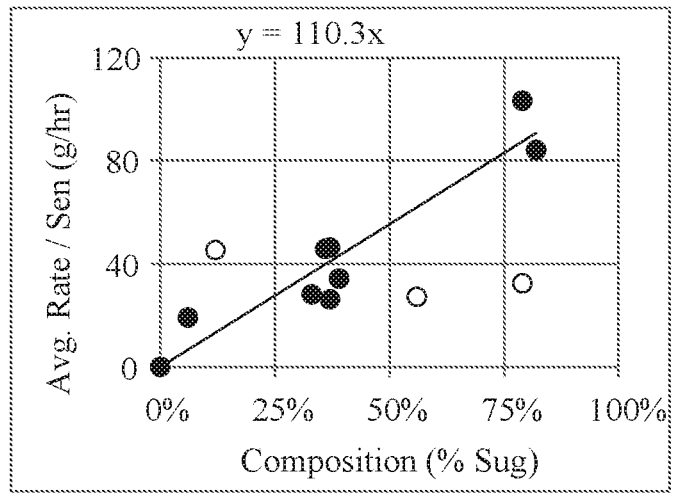

FIGS. 18A-18C show examples of patterns and relationships between sigmoid parameters and factors that may be used to estimate sigmoid parameters for one individual. Sigmoid parameters may be used to make temporal predictions. For modeling food an increasing sigmoid form may be used. FIG. 18A shows a plot of the sigmoid scale parameter, $C_p$, and carbohydrate intake. For this individual, the slope of the $C_p$-vs-carbohydrate line is sensitivity to carbohydrates, 2.8 (mg/dL/g of carbohydrate). FIG. 18B shows a plot of sigmoid location parameter, $L_p$, and food composition, percent sugar. The negative slope of the $L_p$-composition relationship indicates that glucose rise occurs earlier with increasing sugar content. FIG. 18C shows a plot of an intermediate parameter, ratio of average glycemic rate to carbohydrate sensitivity, Eqs. 2A-2F, and food composition, percent sugar. The apparent relationship between the ratio average glycemic rate to carbohydrate sensitivity and composition may be used to estimate the sigmoid shape parameter, Sp for this person.

Figure 19A:
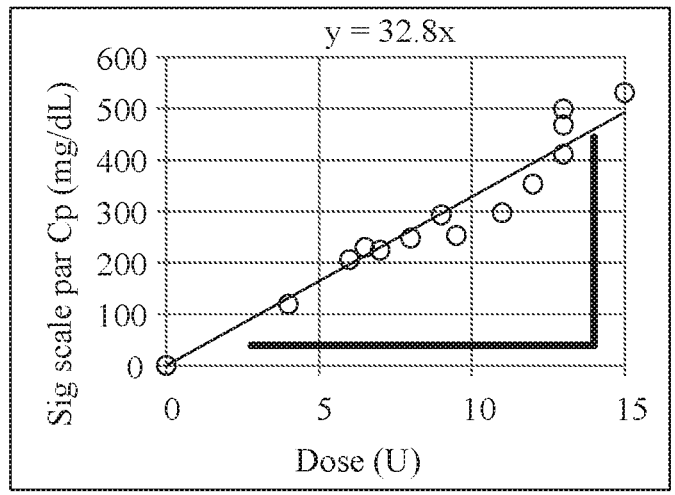
FIGS. 19A-19C show examples of relationships between factors and parameters of sigmoid forms used to create a model of an individual's glycemic response to insulin.
Figure 19B:
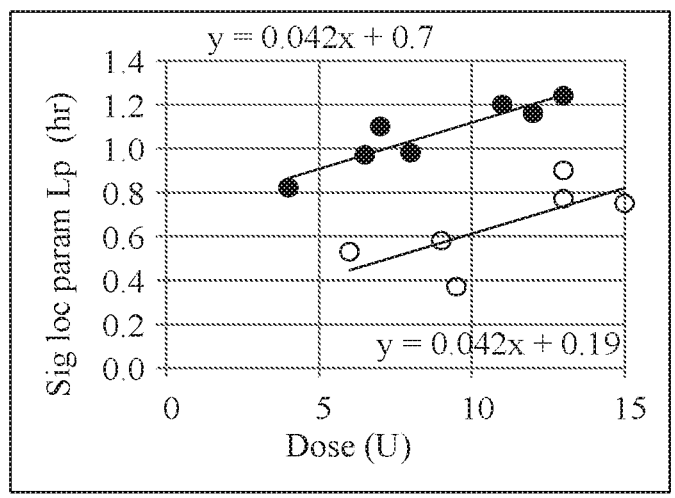
Figure 19C:
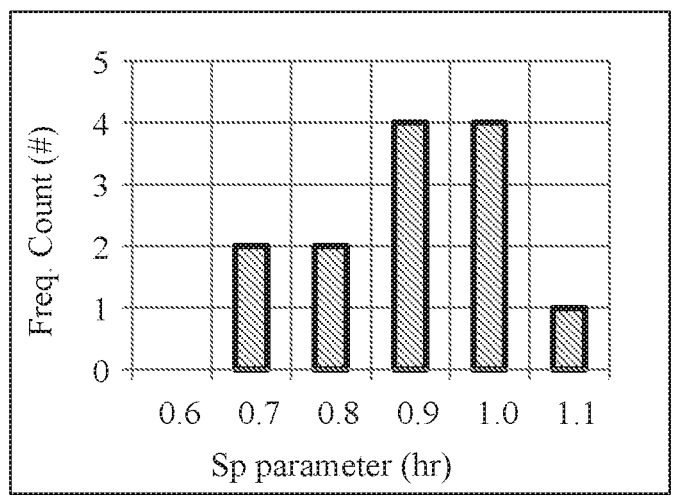
Figure 20A:
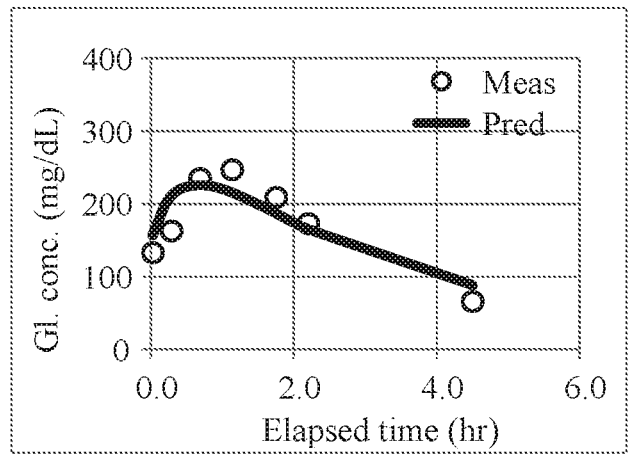
FIGS. 20A-20F show glycemic responses, measured and predicted.
Figure 20B:
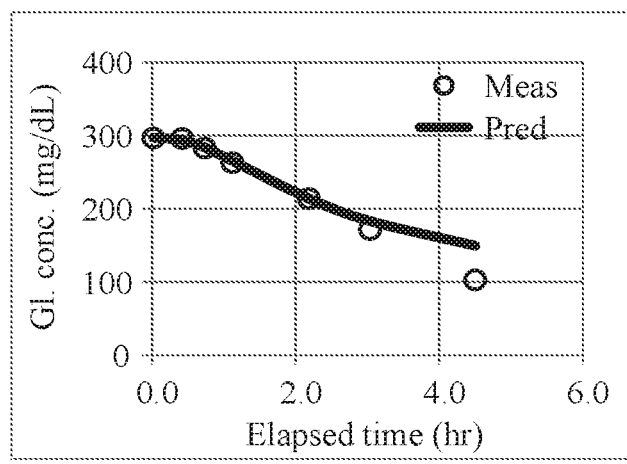
Figure 20C:
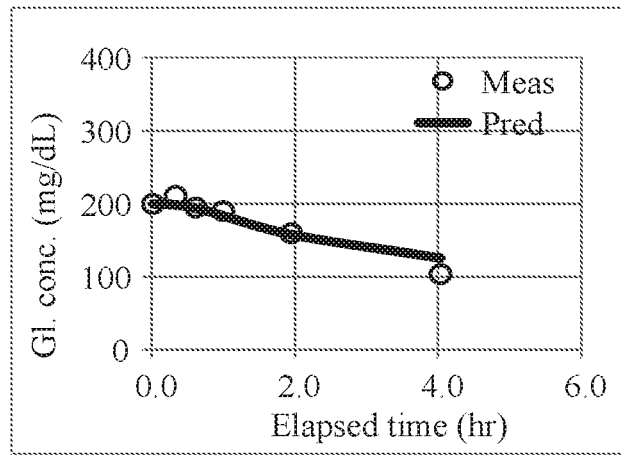
Figure 20D:
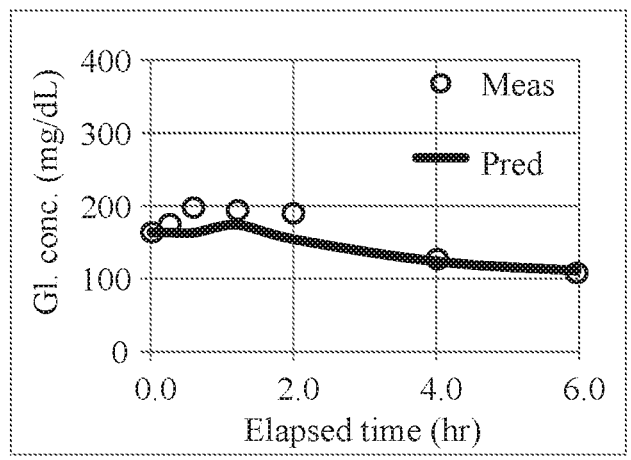
Figure 20E:
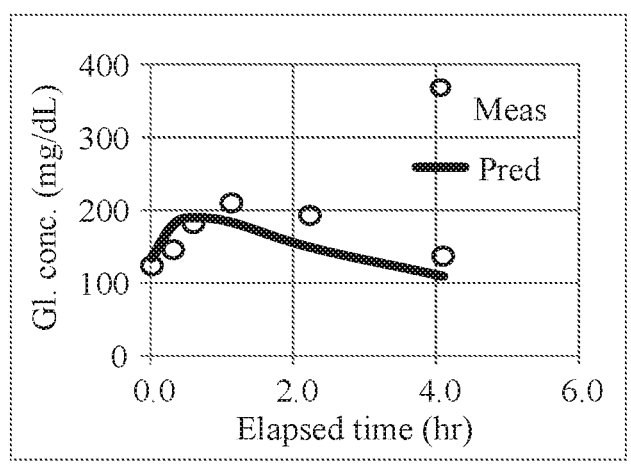
Figure 20F:
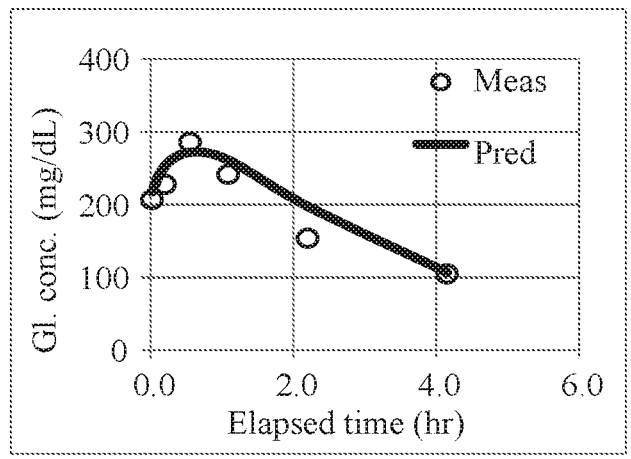

FIG. 19A-19C show examples of patterns and relationships between sigmoid parameters and factors that may be used to estimate sigmoid parameters for an individual. Sigmoid parameters may be used to make temporal predictions. For modeling medication response a decreasing sigmoid form may be used. FIG. 19A shows a plot of the sigmoid scale parameter, $C_p$, and insulin received. For this individual, the slope of the $C_p$-vs-dosage line is sensitivity to insulin, 32.8 (mg/dL/U of the applied insulin). FIG. 19B shows a plot of sigmoid location parameter, $L_p$, and dosage. The positive slope of the $L_p$-dosage relationship indicates that the effect of insulin on glucose peaks later with increasing dosage. FIG. 19C shows a histogram plot of Sp for insulin as metabolized by a person. The histogram indicates the count of occurrences, for example histogram of data from FIG. 17, col 23, there were 4 occurrences of $S_p$ values between 0.85 and 0.95.

FIGS. 20A-20F show predicted glycemic responses for several meals of a person, and measured glycemic responses are also shown on these plots. A metabolic model was created using the method 200 above and logged data was transformed to reveal patterns used to estimate parameters that were then used to predict temporal responses. The data in FIGS. 20A-20F show data from a person having Type 1 diabetes for 27 years that logged meal data, medication data, and blood glucose levels for various meals. Activity was not logged or modeled. Blood glucose was measured with a BGM and food and medicine logs were comprised of timing, quantity, and composition. Data for meals similar to those shown in FIGS. 20A-20F where collected and models created. The predicted value curves shown in FIGS. 20A-20F were not created using the measured data shown in FIGS. 20A-20F. In other words, FIGS. 20A-20F show predicted value curves created with a first set of data and a second set of data validating the predicted value curves.

Model construction and application where as follows:

A subject logged glucose, food, and medication for 14 meals (activity was not logged or modeled). Information from these logs is found in FIGS. 13 and 15A-15C. Food and medication log data were summarized before fitting sigmoid forms to the data. Food summary data for the 14 meals is found in FIG. 14.

A sigmoid form was assumed for modeling the data. To estimate sigmoid parameters, measured responses were fitted to sigmoid forms according to Eq. 1A-1C and a minimizing sum of squared errors using a non-linear solver was used. Responses were assumed to be composed of one or more sigmoid effect(s); increasing, decreasing, or both. To estimate sigmoid parameters by fitting, sigmoid parameters were calculated using Eq. 1A-1C and the data was fitted to the sigmoid forms of a cumulative log normal probability function (see FIGS. 6A-6C and 16).

For each entry in the medicine or the food log, a corresponding sigmoid form was fitted. Fitted responses were calculated according to Eq. 1A-1C and minimizing the sum of the squared errors between fitted and measured responses was implemented. One decreasing sigmoid effect was fitted to one insulin dose, and one increasing sigmoid effect was fitted to one sitting of ingested food.

$$\text{Response} = \Sigma \text{Effects}_i + \Sigma \text{Interactions} \qquad \text{Eq. 1A}$$

$$\text{Incr.Sigmoid}_i \text{Effect(time)} = Cp_i \times \text{Sigmoid Form(time}, Lp_i, Sp_i) \qquad \text{Eq. 1B}$$

$$\text{Decr.Sigmoid}_i \text{ Effect(time)} = Cp_i \times \text{Sigmoid Form(time}, Lp_i, Sp_i) \qquad \text{Eq. 1C}$$

Food log entries may be combined, or medication dose log entries may be combined when forming models based on quantities, time differences, and metabolic form parameters, such as the sigmoid parameters location and shape parameters.

Errors were computed by subtracting the measured responses from the corresponding fitted response, errors were then squared and summed.

A generalized reduced gradient non-linear solver was used to estimate sigmoid parameter values by minimizing the sum of the squared errors. Boundaries may be placed on the solution space for instance insulin sensitivity, etc. This procedure for determining parameter estimates was performed on data from each meal. The results from the fitting procedure are listed in FIG. 17 with summary of food and dose logs.

Example 1

To create and apply a predictive model, in this example useful relationships were created using data in FIG. 17 and the method 200. These relationships can be used to predict sigmoid parameters based on a user's inputs. The estimates of the sigmoid parameters enables prediction of temporal responses. Estimates of the sigmoid parameters $C_p$, $L_p$, and $S_p$ for this non-limiting example are as follows:

Based on inputs, assume a food composition of 40 g of carbohydrate and 50% sugar.

Estimate increasing sigmoid parameters, see FIGS. 18a-18C.

$C_p$, the scale (effect capacity) parameter, is computed as:

$$C_p = 2.78 \text{ mg/dL/g} \times 40 \text{ g}$$

$$C_p = 112 \text{ mg/dL}$$

$L_p$, the location parameter, is estimated as 0.67–2.14 hr/% Su×food composition (% sugar).

$$L_p = 1.0-2.9 \text{ hr/\% } Su \times 50\% \text{ } Su$$

$$L_p = -0.45 \text{ hr}$$

$S_p$, the shape parameter, was estimated using a useful relationship based on a transform which represents a rate at which this individual converts a food composition to glucose.

Values for percent complete and estimated values for $L_p$ were used to estimate $S_p$ as follows:

Using this individual's metabolic relationship between food composition and rate Eq. 2c, the sigmoid shape parameter can be estimated:

$$S_p = \text{Avg rate/Sensitivity}$$

$$S_p = C_p \times A \text{ \%/(time from \%}_1 \text{ to time to \%}_2)/\text{Sensitivity}$$

$$S_p = C_p \times A \text{ \%/\{log normal}^{-1}(70\%, Lp, Sp) - \log \text{ normal}^{-1}(0.01\%, Lp, Sp)\}/\text{Sensitivity}$$

From FIG. 18C, a characteristic relationship of the individual is the rate at which a food composition is converted to glucose as follows:

$$\text{Avg rate/Sensitivity} = 110 \times \% \text{ Sugar}$$

$$= 110 \text{ g/hr/\%} \times 50\%$$

$$= 55 \text{ g/hr}$$

Item 1 and Item 2 are equivalent, therefore $$55 = 112 \times 70\%/\{\log \text{ normal}^{-1}(70\%, -0.45, S_p) - \log \text{ normal}^{-1}(0.01\%, -0.45, S_p)\}/2.8 \text{ g/hr}$$

Solve numerically for $S_p$, a value that makes the approximation true, in this instance:

$$S_p = 2.00 \text{ hr}$$

The individual's response, of the metabolite glucose, to insulin may be characterized and useful relationships shown in FIGS. 18A-18C are as follows:

$C_p$, decreasing sigmoid scale parameter $$C_p = 32.8 \text{ mg/dL/U} \times \text{insulin dose U}$$

Food is expected to increase glucose~112 [mg/dL], therefore dose may be estimated as Calculated dose = 112 mg/dL/32.8 mg/dL/U Calculated dose = 3.5 U $L_p$, decreasing sigmoid location parameter $$L_p = 0.7 \text{ hr.} + 0.04 \text{ hr/U} \times 3.5 \text{ U insulin dose}$$

$L_p$=0.84 hr $S_p$, decreasing sigmoid shape parameter $L_p$=0.84 hr

The predicted temporal response for this individual is summarized by the parameter estimates:

Increasing sigmoid parameters:

$C_p$ —112 mg/dL $L_p$ — −0.45 hr $S_p$ —2.00 hr

Decreasing sigmoid parameters:

$C_p$ —112 mg/dL $L_p$ —0.84 hr $S_p$ —0.84 hr

The results of fitted sigmoid forms using the above parameters are shown in FIGS. 20A-20F for data not used to create the models or during regression analyses.

Statistical software such as R, Statistica, IMP/SAS, SPSS, Minitab and others may be used to construct statistical models. In the examples disclosed herein, partial least squares (PLS), a statistical algorithm sometimes used in machine learning, were used to estimate sigmoid parameters which were then used to predict temporal responses.

Example 2

The PLS method was applied to data shown in FIG. 17. The model generation related food and dosage to sigmoid parameters and did not utilize transforms. However, transforms may be used with statistical methods as disclosed herein. As disclosed, a simple PLS regression model was constructed relating food composition and insulin to sigmoid parameters. Other activities such as exercise can be recorded and used in modeling. From the 14 meal data shown in FIG. 17, ten meals with increasing and decreasing sigmoid effects were used to create a model. To balance predictive reliability and accuracy of a regression model, 3 of 10 meals were randomly selected and used to train and cross validate the model.

Component selection for inclusion in the model was based on predicted residual sum of squares (PRESS), a statistical method that can be used to balance the accuracy and reliability of trained predictive models. This modeling procedure was repeated multiple times resulting in multiple models whose temporal predictions were combined. Models were constructed from different groupings of 7 meals for modeling and 3 meals for validation, all from the same data set of 10 meals.

The factors included in the PLS model were:

Food factors from food log summary: sugar (g), starch (g), fat (g), and protein (g).

Dosage factors from medicine log summary: Dose (U).

Factor combinations from the food and medicine log summaries:

Su/SSF Sugar (g)/(Sugar (g)+Starch (g)+Fat (g))

St/SSF Starch (g)/(Sugar (g)+Starch (g)+Fat (g))

(Sugar (g)+Starch (g))/Dose (U) ratio of carbohydrate intake to insulin intake.

A second order polynomial fit was used in the PLS model of FIG. 21. The PLS coefficient matrices represent a relationship between sigmoid parameters and regression factors.

FIG. 21 shows the application of the combined trained PLS models to 4 meals where:

The sigmoid parameters location and shape were estimated using a regression coefficient matrix and a factor value matrix for food composition, quantity, and insulin dose for each of the four meals.

The meals used for testing predictions were not used to construct the PLS models. Predictions from applying the PLS model(s) to meals 16, 22, 34, and 39 are shown in FIG. 21, and are summarized in a plot of measured versus predicted values for these four meals.

In creating the models additional information from that found in the various figures herein may also be used such as calorie, fiber, vitamin and mineral content, other nutritional data, cost, preferences, and other information. This additional data can be used in constructing modeled meals rather than constructing models.

Figure 22:
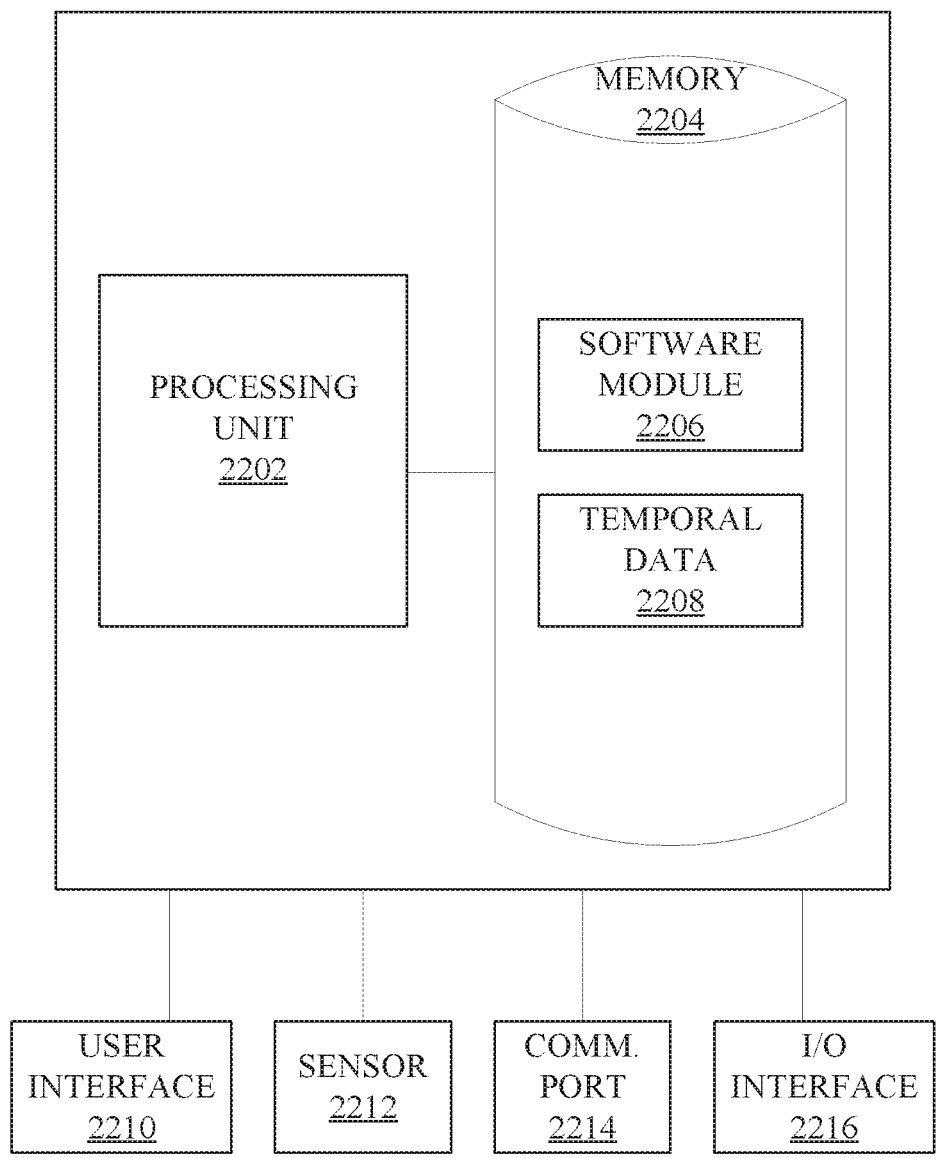
FIG. 22 shows an example of a computing device.

FIG. 22 shows an example schematic of computing device 220. Computing device 2200 may include portable computing device 106 or remote computing device 116 described herein. As shown in FIG. 22, computing device 2200 may include a processing unit 2202 and a memory unit 2204. Memory unit 2204 may include a software module 2206 and temporal data 2208. While executing on processing unit 2202, software module 2204 may perform processes for creating predictive models and providing recommendations, including, for example, one or more stages included in the method 200 described herein.

Temporal data 2208 may include the various data described herein such as medications, dosage, food information such as sugar and carbohydrate levels, activity data, user data such as age, weight, height, activity levels, etc.

Computing device 2202 may also include a user interface 2210. User interface 2210 can include any number of devices that allow a user to interface with computing device 2200. Non-limiting examples of user interface 2200 include a keypad, a microphone, a speaker, a display (touchscreen or otherwise), etc.

Computing device 2200 may also include a sensor 2212. Sensor 2212 can include any number of devices that provides information to allow computing device 2212 to information that may be used for creating and implementing predictive models as disclosed herein. A non-limiting example of sensor 202 includes a glucose sensor.

Computing device 2200 may also include a communications port 2214. Communications port 2214 may allow computing device 2200 to communicate with information systems, glucose meters, and other devices as disclosed herein. Non-limiting examples of communications port 2214 include, Ethernet cards (wireless or wired), Bluetooth® transmitters and receivers, near-field communications modules, etc.

Computing device 2200 may also include an input/output (I/O) device 2216. I/O device 2216 may allow computing device 2216 to receive and output information. Non-limiting examples of I/O device 2216 include, a camera (still or video), a printer, a scanner, etc.

Computing device 2200 may be implemented using a personal computer, a network computer, a mainframe, a handheld device, a personal digital assistant, a smartphone, glucose monitors, insulin pumps, or any other similar microcomputer-based workstation. Computing device 2200 may be located in close proximity to the various systems described herein. Computing device 2200 may also be remote from the various systems described herein.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. A method comprising:
   receiving, at a computing device, comprising a processor, an indication of a food, a medication, or a combination of food and medication to be ingested;
   identifying, by the computing device, a metabolic rate for the food, the medication, or the combination of food and medication to be ingested;
   formulating, by the computing device, a model for predicting, a metabolite level change based on the metabolic rate for the food, the medication, or the combination of food and medication to be ingested, the model including variables corresponding to the food, the medication, or the combination of food and medication to be ingested;
   validating the model against a subsample of temporal data not used to formulate the model;
   storing the model on a data storage device;
   receiving, at the computing device, a behavior, the behavior input including an indication of an ingestion of the food, the medication, or the combination of food and medication to be ingested;
   determining, by the computing device, a metabolite level change based at least in part on the model;
   selecting, by the computing device, a recommended behavior; and
   outputting the recommended behavior to a display associated with the computing device.

2. The method of claim 1, wherein the metabolic rate for the food, the medication, or the combination of food and medication to be ingested includes an absolute value for glucose.

3. The method of claim 1, wherein the metabolic rate for the food, the medication, or the combination of food and medication to be ingested includes an increase in a blood glucose level.

4. The method of claim 1, wherein the metabolic rate for the food, the medication, or the combination of food and medication to be ingested includes a decrease in a blood glucose level.

5. The method of claim 1, wherein the temporal data includes exercise activities that change a blood glucose level.

6. The method of claim 1, wherein the temporal data includes the metabolite levels recorded over a time interval.

7. The method of claim 1, wherein the model is formulated according to at least one of a statistical analysis, a Monte Carlo simulation, a single variable regression analysis, and a multivariable regression analysis.

8. The method of claim 1, wherein receiving the temporal data includes receiving updated temporal data, the method further comprising:
   identifying an updated metabolic rate based on metabolite levels extracted from the updated temporal data; and
   wherein validating the model includes validating the model against the updated metabolic rate.

9. The method of claim 8, further comprising formulating a new model when the model does not validate against the updated metabolic rate.

10. The method of claim 1, wherein the recommended behavior includes two or more coupled metabolic effects.

11. A system comprising:
    a display;
    a processor in electrical communication with the display; and
    a memory that store instructions that, when executed by the processor, cause the processor to perform operations comprising:
    receiving an indication of a food, a medication, or a combination of food and medication to be ingested,
    identifying a metabolic rate for the food, the medication, or the combination of food and medication to be ingested,
    formulating a model for predicting a metabolite level change based on the metabolic rate for the food, the medication, or the combination of food and medication to be ingested,
    the model including variables corresponding to the food, the medication, or the combination of food and medication to be ingested,
    validating the model against a subsample of temporal data not used to formulate the model,
    storing, to the memory, the model,
    receiving a behavior input, the behavior input including an indication of an ingestion of the food, the medication, or the combination of food and medication to be ingested,
    determining a metabolite level change based at least in part on the model,
    selecting a recommended behavior, and
    outputting the recommended behavior to a display associated with the completing device.

12. The system of claim 11, wherein the metabolic rate for the food, the medication, or the combination of food and medication to be ingested includes an absolute value for glucose and an increase in a blood glucose level.

13. The system of claim 11, wherein the metabolic rate for the food, the medication, or the combination of food and medication to be ingested includes a decrease in a blood glucose level.

14. The system of claim 11, wherein the temporal data includes exercise activities engaged in by the user that result in a change in a blood glucose level.

15. The system of claim 11, wherein the temporal data includes the metabolite levels recorded over a time interval.

16. The system of claim 11, wherein the model is formulated according to at least one of a statistical analysis, a Monte Carlo simulation, a single variable regression analysis, and a multivariable regression analysis.

17. The system of claim 11, wherein receiving the temporal data includes receiving updated temporal data, the method further comprising: identifying an updated metabolic rate based on metabolite levels extracted from the updated temporal data; and wherein validating the model includes validating the model against the updated metabolic rate.

18. The system of claim 17, further comprising formulating a new model when the model does not validate against the updated metabolic rate.

19. The system of claim 11, wherein the recommended behavior includes two or more coupled metabolic effects.

20. The system of claim 11, wherein the system is one of a blood glucose meter, an infusion pump, and a smartphone.

21. A computing device comprising:
a processor;
a memory communicatively coupled to the processor;
a display including an interface that includes inputs to the computing device, the inputs including one or more of the following:
   an ingested food input specifying a quantity of mass, a percent a composition, or combinations of these;
   a drug dose input specifying a quantity (Units) and composition; and
   an activity or exercise input—intensity (composition) and duration; and
a model stored in the memory for predicting a metabolite level change based on the inputs at the interface, including the metabolic rate for the food, the medication, or the combination of food and medication to be ingested, and the activity or exercise input;
the interface at the display also including outputs the prediction from the model, the outputs including one or more of the following:
   a predicted time course for glycemic responses to glycemic events, a time to metabolize ingested food;
   a time to metabolize medication; and
   a duration of time to an activity's effect on a dose or doses of medicine.

22. The computing device of claim 21 wherein the duration of an activity's effect on a dose or doses of medicine is a time to 50% of effect.

23. The computing device of claim 21 wherein the duration of an activity's effect on a dose or doses of medicine is a time to 25% of effect.

24. The computing device of claim 21 wherein the duration of an activity's effect on a dose or doses of medicine is a time to 75% of effect.

25. The method of claim 21 wherein the duration of an activity's effect on a dose or doses of medicine indicates the status of an effect on board based on a dose or doses of medicine.

26. The method of claim 21 wherein the prediction from the model is used to estimate an effect's time to a percentage complete between 0.1 to 99.9 percent complete.

27. The method of claim 21 wherein the prediction from the model is used to indicate the effects on board from at least one of food, medication, or activity.

28. The method of claim 21 wherein the prediction from the model is used to indicate the effects on board for a combination of food, medication, and activity.

29. The method of claim 21 wherein the display is interactive and receives change inputs for changes in food, activity, and or medication and uses the model for predicting a metabolite level change based on the change inputs for the metabolic rate characteristic for the food, the medication, or the combination of food and medication to be ingested, and an activity and activity level.

30. The computing device of claim 21, further comprising an input for one or more goals, and an output for one or more recommended behaviors which are related to the one or more goals.

31. The computing device of claim 21, further comprising collecting data for modeling glycemic response from devices and or apps, from one or more of the following: glucose data, medication data, fitness and or health monitor data, and food logging data.

32. The computing device of claim 31, further comprising generating reports from collected data for modeling glycemic response, for effects including but not limited to:
   food and medication: sensitivity including characteristics rate, effect capacities;
   activity including change in medication sensitivity, duration of elevated medication sensitivity; or
   model performance.

33. The method of claim 1, further comprising inputting one or more goals, the recommended behavior output to a display associated with the computing device considering the one or more goals in making the recommended behavior output.

34. The system of claim 11 wherein the processor receives an indication of at least one goad, Wherein selecting a recommended behavior is based on the at least one goal.

* * * * *